(12) United States Patent
Murata et al.

(10) Patent No.: US 8,158,560 B2
(45) Date of Patent: Apr. 17, 2012

(54) INSECTICIDAL ARYLPYRROLINE COMPOUNDS

(75) Inventors: Tetsuya Murata, Oyama (JP); Masashi Ataka, Oyama (JP); Yasushi Yoneta, Hanyu (JP); Hidekazu Watanabe, Oyama (JP); Eiichi Shimojo, Oyama (JP); Katsuhiko Shibuya, Shimotsuke (JP); Teruyuki Ichihara, Oyama (JP)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/941,501

(22) Filed: Nov. 8, 2010

(65) Prior Publication Data

US 2011/0118319 A1    May 19, 2011

Related U.S. Application Data

(60) Provisional application No. 61/258,811, filed on Nov. 6, 2009.

(30) Foreign Application Priority Data

Nov. 6, 2009   (EP) ..................... 09175276

(51) Int. Cl.
- *A01N 43/36* (2006.01)
- *A61K 31/402* (2006.01)
- *C07D 207/20* (2006.01)

(52) U.S. Cl. ............ 504/283; 514/428; 548/565
(58) Field of Classification Search ............ None
See application file for complete search history.

(56) References Cited

U.S. PATENT DOCUMENTS

| 2010/0179194 A1 | 7/2010 | Mihara et al. |
| 2010/0216792 A1 | 8/2010 | Görgens et al. |
| 2010/0298558 A1 | 11/2010 | Mita et al. |
| 2011/0071141 A1 | 3/2011 | Murata et al. |

FOREIGN PATENT DOCUMENTS

| JP | 2008-133273 A | 6/2008 |
| WO | WO 2009/072621 A1 | 6/2009 |
| WO | WO 2009/080250 A2 | 7/2009 |
| WO | WO 2009/097992 A1 | 8/2009 |
| WO | WO 2010/020522 A1 | 2/2010 |

OTHER PUBLICATIONS

Pitt, G.R.W., et al., "Non-peptide oxytocin agonists," *Bioorganic & Medicinal Chemistry Letters* 14:4585-4589, Elsevier Ltd., United Kingdom (2004).
Unverified English language translation of Japanese Patent Application Publication JP 2008-133273, published Jun. 12, 2008.
European Search Report for European Application No. EP 09 17 5276, European Patent Office, Germany, search completed Mar. 18, 2010.
International Search Report for International Application No. PCT/EP2010/066741, European Patent Office, Rijswijk, Netherlands, mailed Feb. 28, 2011.

*Primary Examiner* — Yong Chu
*Assistant Examiner* — Michael Barker
(74) *Attorney, Agent, or Firm* — Sterne, Kessler, Goldstein & Fox P.L.L.C.

(57) ABSTRACT

The present invention relates to novel arylpyrrolines having the formula (I) and their use as insecticides, as well as to processes for the preparation of the arylpyrrolines

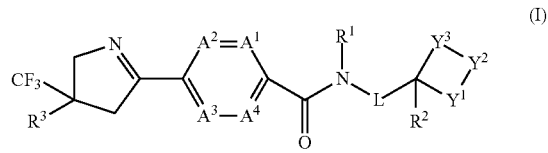

wherein L, $A^1$ to $A^4$, $Y^1$ to $Y^3$, $R^1$ to $R^3$ are as defined in the specification of the patent application.

12 Claims, No Drawings

INSECTICIDAL ARYLPYRROLINE COMPOUNDS

The present invention relates to novel arylpyrrolines and their use as insecticides, as well as to processes for the preparation of the arylpyrrolines.

Japanese Patent Application No. 2007-283820, published as JP2008-133273 A, and WO 2009/072621 describe certain pyrroline compounds having insecticidal properties. WO 2009/080250, which is directed to arylisoxazoline type compounds having insecticidal properties, describes certain arylisoxazoline compounds having as a structural element or substituent a tetracyclic group, in particular a sulfur-containing four membered ring connected to the nitrogen atom of the amide group. WO 2010/020522 which is directed to arylisoxazoline type compounds, whereas the arylisoxazoline ring is substituted. WO2010/020522 discloses in table 1 also four specific pyrroline type compounds, namely compounds A46, A47, A48 and A49. These compounds have been excluded from the present invention.

Since ecological and economic demands on modern plant treatment agents are continually increasing, particularly in respect to the amount applied, residue formation, selectivity, toxicity and favorable production methodology, and also because, for example, resistance problems can occur, there is the on-going task to develop new plant treatment agents that at least in certain areas are able to demonstrate advantages over known agents.

The inventors of the present invention devotedly conducted research to create a novel compound exhibiting higher effects and having a wide spectrum as an insecticide. As a result they found novel arylpyrrolines, which exhibit high activity, a wide spectrum and safety, and, furthermore, are effective against pests that are resistant to organic phosphorus agents or carbamate agents.

Thus, this invention is directed to arylpyrroline compounds of formula (I) or a salt or N-oxide thereof,

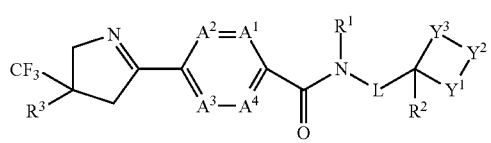

wherein
- $A^1$, $A^2$, $A^3$ and $A^4$ independently represent a group C—H, C—$R^4$, or nitrogen;
- L stands for a single bond, —$CH_2C(O)NH$—, $C_1$-$C_8$alkylene, $C_1$-$C_8$haloalkylene, $C_2$-$C_8$alkenylene, $C_2$-$C_8$haloalkenylene, $C_2$-$C_8$alkynylene, or $C_2$-$C_8$haloalkynylene, preferably a single bond, —$CH_2C(O)NH$—, $C_1$-$C_6$alkylene, $C_1$-$C_6$haloalkylene, more preferably a single bond, —$CH_2C(O)NH$—, or $C_1$-$C_2$alkylene, most preferably a single bond, —$CH_2C(O)NH$—, or methylene;
- $R^1$ stands for hydrogen, $C_1$-$C_8$alkyl, $C_1$-$C_8$alkylcarbonyl, or $C_1$-$C_8$alkoxycarbonyl, preferably hydrogen, methyl, ethyl, methylcarbonyl, or methoxycarbonyl, more preferably hydrogen, methyl or ethyl, most preferably hydrogen or methyl;
- $R^2$ stands for hydrogen, or $C_1$-$C_8$alkyl, preferably hydrogen or methyl, most preferably hydrogen;
- $R^3$ stands for aryl or aryl substituted by one to four X, or heterocyclyl or heterocyclyl substituted by one to three X; preferably $R^3$ stands for phenyl or phenyl substituted by one to four X, pyridyl or pyridyl substituted by one to three X, preferably stands for 3,5-dichlorophenyl, 3,4,5-trichlorophenyl, 3,5-bis-(trifluoromethyl)phenyl, 2,6-dichloro-pyridin-4-yl or 2,6-bis-(trifluoromethyl)pyridin-4-yl;
- $Y^1$, $Y^2$ and $Y^3$ independently of another stand for $CR^5R^6$, C=O, C=N—$OR^7$, N—$R^7$, S(O)$_n$ wherein n stands for 0, 1, or 2 (i.e. a group S, SO, $SO_2$) S=N—$R^7$ or S(O)=N—$R^7$; $Y^1$, $Y^2$ and $Y^3$ are not $CR^5R^6$ at the same time;
- $R^4$ independently stands for halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$ alkoxy, $C_1$-$C_8$haloalkoxy, $C_1$-$C_8$ alkoxycarbonyl, ary or aryl optionally substituted by one to three $R^8$, or heteroaryl or heteroaryl optionally substituted by one to three $R^8$, or where two $R^4$ are adjacent, the two $R^4$ may together with the carbon atoms to which they are bound form a 5-membered ring, wherein the 5-membered ring consists of one of the following groups —OCH=N—, —SCH=N—, —OCR$^8$=N—, or —SCR$^8$=N—, preferably $R^4$ stands for halogen, cyano, nitro, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, or $C_1$-$C_6$alkoxycarbonyl, more preferably $R^4$ stands for halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, most preferably $R^4$ stands for bromo, chloro, fluoro, cyano, nitro, methyl, ethyl, trifluoromethyl, methoxy, difluoromethoxy, trifluoromethoxy, or methoxycarbonyl;
- X independently stands for halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl; preferably X stands for bromo, chloro, fluoro, cyano, nitro, methyl, ethyl, trifluoromethyl, methoxy, difluoromethoxy, trifluoromethoxy, or methoxycarbonyl, more preferably for bromo, chloro, fluoro, cyano, nitro, methyl, ethyl, trifluoromethyl, methoxy, or trifluoromethoxy, most preferably for trifluoromethyl, bromo, chloro, or fluoro;
- $R^5$ and $R^6$ independently of each other stand for hydrogen, halogen, $C_1$-$C_8$alkyl, or $C_1$-$C_8$haloalkyl; preferably stand for hydrogen or methyl, most preferably for hydrogen;
- $R^7$ stands for hydrogen, cyano, nitro, $C_1$-$C_8$alkyl, $C_1$-$C_8$haloalkyl, $C_3$-$C_6$-cycloalkyl-$C_1$-$C_4$alkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$ alkylsulfonyl, $C_1$-$C_8$haloalkylsulfonyl, aryl-$C_1$-$C_4$alkyl or aryl $C_1$-$C_4$alkyl wherein the aryl moiety is substituted by one to three $R^9$, or heteroaryl-$C_1$-$C_4$alkyl or heteroaryl-$C_1$-$C_4$allyl wherein the heteroaryl moiety is substituted by one to three $R^9$; $R^7$ preferably stands for hydrogen, methyl, ethyl, 2,2,2-trifluoroethyl, cyclopropylmethyl, methylcarbonyl, trifluoromethylcarbonyl, methoxycarbonyl, trifluoromethoxycarbonyl, methylsulfonyl, trifluoromethylsulfonyl, benzyl or benzyl wherein the phenyl moiety is substituted by one to three $R^8$, $R^7$ more preferably stands for hydrogen, methyl, 2,2,2-trifluoroethyl or benzyl;
- $R^8$ stands for halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl; preferably $R^8$ stands for bromo, chloro, fluoro, cyano, nitro, methyl, ethyl, trifluoromethyl, methoxy, difluoromethoxy, trifluoromethoxy, or methoxycarbonyl, more preferably for chloro, fluoro, cyano, nitro, methyl, ethyl, trifluoromethyl, methoxy, or trifluoromethoxy, most preferably for bromo, chloro, or fluoro; and $R^9$ stands for hydrogen, halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl, preferably for hydrogen, bromo, chloro, fluoro, cyano, nitro, methyl, ethyl, trifluoromethyl, methoxy, difluoromethoxy, trifluoromethoxy, or methoxycarbonyl, more preferably for hydrogen, chloro, fluoro, cyano, nitro, methyl, ethyl, trifluoromethyl, methoxy, or trifluoromethoxy, most preferably for hydrogen, bromo, chloro, or fluoro.

The present invention does not include the compounds A46, A47, A48 and A49 disclosed in table 1 of WO 2010/020522, namely compound Excl-1 (=A46): The compound of formula (I) wherein $R^3$ is 3,5-dichlorophenyl, $A^1$ is C—$CH_3$, $A^2$, $A^3$ and $A^4$, each stand for C—H, $R^1$ is H, L is a single bond, $Y^1$ and $Y^3$ each stand for $CH_2$, $Y^2$ is $SO_2$, and $R^2$ is H;

compound Excl-2 (=A47): The compound of formula (I) wherein $R^3$ is 3,5-dichlorophenyl, $A^1$ is C—$CH_3$, $A^2$, $A^3$ and $A^4$, each stand for C—H, $R^1$ is H, L is a single bond, $Y^1$ and $Y^3$ each stand for $CH_2$, $Y^2$ is S, and $R^2$ is $CH_3$;

compound Excl-3 (=A48): The compound of formula (I) wherein $R^3$ is 3,5-dichlorophenyl, $A^1$ is C—$CH_3$, $A^2$, $A^3$ and $A^4$, each stand for C—H, $R^1$ is H, L is a single bond, $Y^1$ and $Y^3$ each stand for $CH_2$, $Y^2$ is SO, and $R^2$ is H;

compound Excl-4 (=A49): The compound of formula (I) wherein $R^3$ is 3,5-dichlorophenyl, $A^1$ is C—$CH_3$, $A^2$, $A^3$ and $A^4$, each stand for C—H, $R^1$ is H, L is a single bond, $Y^1$ and $Y^3$ each stand for $CH_2$, $Y^2$ is S, and $R^2$ is H.

If not defined otherwise, the term "alkyl" used either alone or combined with other terms such as "aminoalkyl" or "haloalkyl" includes straight-chained or branched alkyl containing up to 8 carbon atoms, such as methyl, ethyl, n- or iso-propyl; n-, iso-, secondary- or tertiary-butyl; n-pentyl, n-hexyl, n-heptyl, n-octyl, n-nonyl, n-decyl, n-undecyl or n-dodecyl, and preferably stands for alkyl having 1 to 6 carbon atoms.

If not defined otherwise, the term "alkenyl" used either alone or combined with other terms preferably stands for alkenyl having 2 to 8 or 2 to 5 carbon atoms. Examples include vinyl, allyl, 1-propenyl, 1-, 2-, or 3-butenyl or 1-pentenyl. More preferred it stands for alkenyl having 2 to 4 carbon atoms.

If not defined otherwise, the term "alkynyl" used either alone or combined with other terms preferably stands for alkynyl having 2 to 6 or 2 to 5 carbon atoms. Examples include ethynyl, propargyl, 1-propynyl, but-3-ynyl or pent-4-ynyl. More preferred it stands for alkynyl having 2 to 4 carbon atoms.

If not defined otherwise, the term "halogen" or "halo" used either alone or combined with other terms such as "haloalkyl" includes fluorine, chlorine, bromine and iodine.

If not defined otherwise, the term "haloalkyl" used either alone or combined with other terms stands for alkyl groups which are partially or fully substituted with halogen atoms which may be the same or different. Examples of "haloalkyl" includes among others chemical groups like $CF_3$, $CH_2F$, $CHF_2$, $CH_2CHF_2$, $CCl_3$, $CH_2Cl$, $CHCl_2$, $CF_2CF_3$, $CH_2CF_3$, $CH_2CH_2Cl$, $CH_2CH_2F$, $CHClCH_3$, $CHFCH_3$, $CH_2CHFCl$, $CHCl_2$, $CF_2CF_2H$, and $CH_2CF_3$.

If not defined otherwise, the term "haloalkenyl" used either alone or combined with other terms stands for alkenyl groups which are partially or fully substituted with halogen atoms which may be the same or different. Examples of "haloalk-enyl" includes, among others, chemical groups like 2,2-difluorovinyl, 3,3,3-trifluoro-prop-2-en-1-yl or 4,4,4-trifluoro-but-2-en-1-yl.

If not defined otherwise, the term "haloalkynyl" used either alone or combined with other terms stands for alkynyl groups which are partially or fully substituted with halogen atoms which may be the same or different. Examples of "haloalkynyl" include, among others, chemical groups like 3,3,3-trifluoro-prop-1-en-1-yl or 4,4,4-trifluoro-but-2-en-1-yl.

If not defined otherwise, the term "aryl" used either alone or combined with other terms stands for a ring system which may be mono-, bi- or tricyclic. Examples of such rings include phenyl, naphthalenyl, anthracenyl, indenyl or phenanthrenyl. A preferred aryl group is phenyl.

If not defined otherwise, the term "heteroaryl" used either alone or combined with other terms stands for an aromatic ring containing at least one heteroatom and consisting either of a single ring or of two or more fused rings. Preferably, single rings contain up to three heteroatoms and bicyclic systems up to four heteroatoms which preferably are selected among nitrogen, oxygen and sulfur. Examples of monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, pyridyl is most preferred.

If not defined otherwise, the term "heterocyclyl" is defined to include heteroaryl and in addition their unsaturated or partially unsaturated analogues.

In an [embodiment A], the invention is directed to compounds of formula (I) wherein $A^1$ is C—H or C—$R^4$, $A^2$ is C—H or C—$R^4$, $A^3$ is C—H or C—$R^4$, and $A^4$ is C—H or C—$R^4$, and wherein all other groups are as defined herein.

In an [embodiment B], the invention is directed to compounds of formula (I) wherein $A^1$ is C—$R^4$, $A^2$ is C—H, $A^3$ is C—H, and $A^4$ is C—H, and wherein all other groups are as defined herein.

In an [embodiment C], the invention is directed to compounds of formula (I) wherein $A^1$ is C—H, $A^2$ is C—H, $A^3$ is C—H, and $A^4$ is C—$R^4$, and wherein all other groups are as defined herein.

In an [embodiment D] the invention is directed to compounds as defined in any one of [embodiments A to C], wherein $R^3$ stands for aryl or aryl substituted by one to four X, preferably wherein $R^3$ is phenyl or phenyl substituted by one to four X, more preferably by three X.

In an [embodiment E], the invention is directed to compounds as defined in any one of [embodiments A to C], wherein $R^3$ is selected among 3,5-bis-(trifluoromethyl)-phenyl, 3,5-dibromo-phenyl, 3,5-dichloro-phenyl, 3-trifluoromethyl-phenyl, or 3,4,5-trichloro-phenyl, and 3-chloro-5-trifluoromethyl-phenyl, 3,4-dichloro-5-trifluoromethyl-phenyl.

In an [embodiment F], the invention is directed to compounds as defined in any one of [embodiments A to C], wherein $R^3$ stands for heterocyclyl or heterocyclyl substituted by one to three X, preferably $R^3$ stands for pyridyl or pyridyl substituted by one to three X, preferably stands for 2,6-dichloro-pyridin-4-yl or 2,6-bis-(trifluoromethyl)pyridin-4-yl.

In an [embodiment G], the invention is directed to compounds as defined in any one of [embodiments A to F], wherein $Y^1$, $Y^2$ and $Y^3$ independently of another stands for one of the following chemical groupings $CR^5R^6$, C=O, C=N—$OR^7$, N—$R^7$, $S(O)_n$ wherein n stands for 0, 1, or 2, S=N—$R^7$, or S(O)=N—$R^7$, preferably for $CR^5R^6$, $S(O)_n$ wherein n stands for 0, 1, or 2, S=N—$R^7$, or S(O)=N—$R^7$, $Y^1$, $Y^2$ and $Y^3$ are not $CR^5R^6$ at the same time.

In an [embodiment H], the invention is directed to compounds as defined in any one of [embodiments A to F], wherein $Y_2$ is $S(O)=N-R^7$ or $S(O)_n$ wherein n stands for 0, 1, or 2, and $Y^1$ and $Y^3$ are independently of another $CR^5R^6$.

In an [embodiment I], the invention is directed to compounds having the formula (I-a), wherein $R^1$, $R^2$, $R^4$, $Y^1$, and $Y^3$ are as defined herein; $X^1$, $X^2$, $X^3$ independently of another stands for X, and n stands for 0, 1 or 2; or a salt or N-oxide thereof.

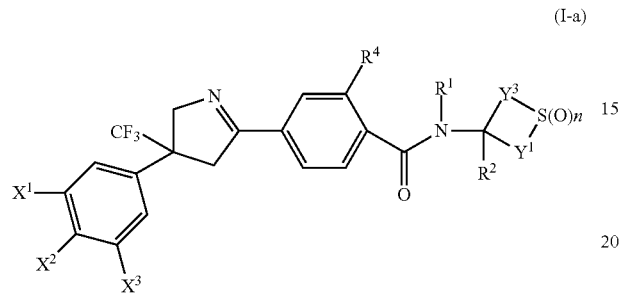

(I-a)

In an [embodiment J], the invention is directed to compounds as defined in [embodiment I] wherein $R^4$ is selected among halogen, $C_{1-4}$alkyl, $C_{1-4}$haloalkyl, preferably among Cl, Br, I, methyl and $CF_3$; $X^1$, $X^2$, $X^3$ independently stands for $C_1$, $CF_3$, Br or H; $Y^1$, $Y^3$ independently stands for $CR^5R^6$ and $R^5$, $R^6$ independently of another stands for H or $C_{1-4}$alkyl, preferably H or methyl.

In an [embodiment K], the invention is directed to compounds having the formula (I-a), wherein $R^1$, $R^2$, $R^4$, $Y^1$, and $Y^3$ are as defined herein; $X^4$, $X^5$ stands for X as defined herein and n stands for 0, 1 or 2, or a salt or N-oxide thereof.

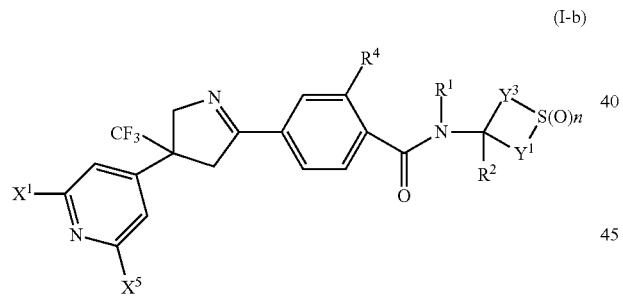

(I-b)

In an [embodiment L], the invention is directed to compounds as defined in [embodiment K] wherein $R^4$ is selected among halogen, $C_{1-4}$alkyl, $C_{1-4}$haloalkyl, preferably stands for Cl, Br, I, methyl or $CF_3$; $X^4$, $X^5$ independently of another stands for Cl, $CF_3$ or H; and $Y^1$, $Y^3$ independently of another stands for $CR^5R^6$, wherein $R^5$ and $R^6$ are as defined herein, preferably as defined in [embodiment J].

In an [embodiment M], the invention is directed to compounds having the formula (I-c),

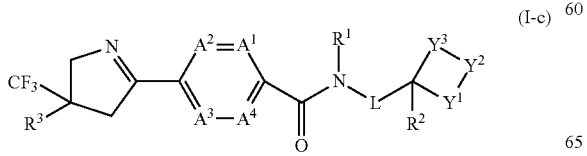

(I-c)

wherein the groups $A^1$ to $A^4$, $R^1$ to $R^3$, and $Y^1$ to $Y^4$ are as defined herein, preferred are compounds of formula (I-c) wherein $A^1$, $A^2$, $A^3$ and $A^4$ independently of another stands for C—H, C—$R^4$, or nitrogen;

L stands for a single bond, —$CH_2C(O)NH$—, $C_1$-$C_6$alkylene, $C_1$-$C_6$haloalkylene, $C_2$-$C_6$alkenylene, $C_2$-$C_6$haloalkenylene, $C_2$-$C_6$alkynylene, or $C_2$-$C_6$haloalkynylene;

$R^1$ stands for hydrogen, $C_1$-$C_6$alkyl, $C_1$-$C_6$alkylcarbonyl, or $C_1$-$C_6$alkoxycarbonyl;

$R^2$ stands for hydrogen, or $C_1$-$C_6$alkyl;

$R^3$ stands for aryl or aryl substituted by one to three substituents X which are independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, or heterocyclyl or heterocyclyl substituted by one to three substituents X which are independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl;

$R^4$ stands for halogen, cyano, nitro, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, or $C_1$-$C_6$alkoxycarbonyl;

$Y^1$, $Y^2$ and $Y^3$ independently of another stands for $CR^5R^6$, $C=O$, $C=N-OR^7$, $N-R^7$, $S(O)_n$ wherein n stands for 0, 1, or 2, $S=N-R^7$, or $S(O)=N-R^7$;

$R^5$ and $R^6$ independently of another stands for hydrogen, halogen, $C_1$-$C_6$alkyl, or $C_1$-$C_6$haloalkyl;

$R^7$ stands for hydrogen, cyano, $C_1$-$C_6$alkyl, $C_1$-$C_6$haloalkyl, $C_3$-$C_6$-cycloalkyl-$C_1$-$C_4$alkyl, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkyl-sulfonyl, $C_1$-$C_6$haloalkylsulfonyl, aryl-$C_1$-$C_4$alkyl-, or aryl-$C_1$-$C_6$alkyl wherein the aryl moiety is substituted by one to three substituents $R^9$ which is independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, heteroaryl-$C_1$-$C_4$alkyl, or heteroaryl-$C_1$-$C_4$alkyl wherein the heteroaryl moiety is substituted by one to three substituents $R^9$ which is independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl; or a salt or N-oxide thereof.

It is understood that the compounds Excl-1, Excl-2, Excl-3, and Excl-4 as defined before, are also excluded in the embodiments according to the invention, in particular [embodiments A to M].

The invention is further directed to intermediate compounds having the formula (II) which may be used for the preparation of the compounds according to the invention.

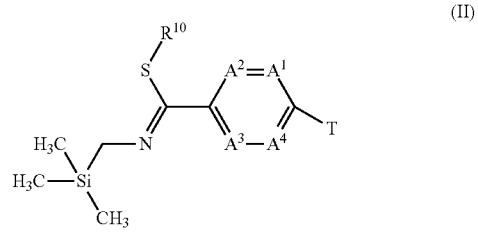

(II)

wherein $A^1$, $A^2$, $A^3$, and $A^4$ are as defined herein;
$R^{10}$ stands for hydrogen, or $C_1$-$C_8$ alkyl, preferably hydrogen or methyl;

T stands for CN, methyl, $C_1$-$C_8$alkoxycarbonyl or a chemical group G having the following formula

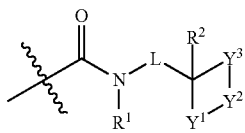

wherein L, $R^1$, $R^2$, $R^4$, $Y^1$, $Y^2$ and $Y^3$ are as defined herein.

Compounds of formula (II) can be prepared according to the methods described in WO 2009/097992.

The invention is moreover directed to a method for the preparation of compounds according to the invention which comprises the steps of reacting the compound of formula (II) as defined before
with a compound of formula (V)

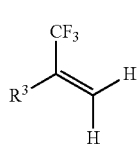

(V)

wherein $R^3$ is as defined herein, in the presence of fluorine reagent such as tetrabutylammonium fluoride in a diluent such as THF.

The compounds according to the present invention show a potent insecticidal action and can therefore be used as an insecticide. Furthermore, the compounds according to the present invention exhibit a strong control effect against harmful insects, without imposing any harmful side effects of drug to cultivated plants. The compounds of the present invention can thus be used for the control of a wide range of pest species, for example, harmful sucking insects, chewing insects, as well as other plant parasitic pests, storage insects, hygiene pests and the like, and can be applied for the purpose of disinfestations and extermination thereof. Harmful animal pest are for example:

As for insects, coleopterans, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus, Aulacophora femoralis*; lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotis fucosa, Galleria mellonella, Plutella maculipennis, Heliothis virescens, Phyllocnistis citrella*; hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental*; orthopterans, for example, *Blatella germanica, Periplaneta americana, Gryllotalpa Africana, Locusta migratoria migratoriodes*; isopterans, for example, *Reticulitermes speratus, Coptotermes formosanus*; dipterans, for example, *Musca domestica, Aedes aegypti, Hylemia platura, Culex pipiens, Anopheles sinensis, Culex tritaeniorhynchus, Liriomyza trifolii*.

As for acari, for example, *Tetranychus cinnabarinus, Tetranychus urticae, Panonychus citri, Aculops pelekassi, Tarsonemus* spp.

As for nematodes, for example, *Meloidogyne incognita, Bursaphelenchus lignicolus* Mamiya et Kiyohara, *Aphelenchoides besseyi, Heterodera glycines, Pratylenchus* spp.

Additionally, the compounds according to the present invention show a good plant tolerance and favourable toxicity to warm-blooded animals and being tolerated well by the environment, and thus are suitable for protecting plants and plant parts.

Application of the compounds of the invention may result in increasing the harvest yields, improving the quality of the harvested material. Additionally, the compounds can be used for controlling animal pests, in particular insects, arachnids, helminths, nematodes and molluscs, which are encountered in agriculture, in horticulture, the field of veterinary medicine, in forests, in gardens and leisure facilities, in the protection of stored products and of materials, and in the hygiene sector. They may preferably be employed as plant protection agents. They are active against normally sensitive and resistant species and against all or some stages of development. These pests include inter alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Arnphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From in the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Mouellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella Z, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material; in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and Cry1F and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds according to the invention at a suitable concentration.

Furthermore, in the field of veterinary medicine, the novel compounds of the present invention can be effectively used against various harmful animal parasitic pests (endoparasites and ectoparasites), for example, insects and helminthes. Examples of such animal parasitic pests include the pests as described below. Examples of the insects include *Gasterophilus* spp., *Stomoxys* spp., *Trichodectes* spp., *Rhodnius* spp., *Ctenocephalides canis, Cimx lecturius, Ctenocephalides felis, Lucilia cuprina*, and the like. Examples of acari include *Ornithodoros* spp., *Ixodes* spp., *Boophilus* spp., and the like.

In the veterinary fields, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as coccidia. Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;* from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi;* from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;* from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides fells, Pulex irritans, Tunga penetrans, Xenopsylla cheopis;* from the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp. (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;* from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschöngastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoae, which attack animals. Animals include agricultural livestock such as, for example, cattle, sheep, goats, horses, pigs, donkeys, camels, buffaloes, rabbits, chickens, turkeys, ducks, geese, cultured fish, honeybees. Moreover, animals include domestic animals—also referred to as companion animals— such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the hosts (when applicable). Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Generally, when used for the treatment of animals the active compounds according to the invention can be applied directly. Preferably they are applied as pharmaceutical compositions which may contain pharmaceutically acceptable excipients and/or auxiliaries which are known in the art.

In the veterinary field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols, unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80% by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

In the present invention, a substance having an insecticidal action against pests including all of these is referred to as an insecticide.

An active compound of the present invention can be prepared in conventional formulation forms, when used as an insecticide. Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), ULV (cold mist, warm mist), and the like.

These formulations can be produced by methods that are known per se. For example, a formulation can be produced by mixing the active compound with a developer, that is, a liquid diluent or carrier; a liquefied gas diluent or carrier; a solid diluent or carrier, and optionally with a surfactant, that is, an emulsifier and/or dispersant and/or foaming agent.

In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like.

The liquefied gas diluent or carrier may be those which are gaseous at normal temperature and normal pressure, for example, aerosol propellants such as butane, propane, nitrogen gas, carbon dioxide and halogenated hydrocarbons.

Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like.

Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like.

Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydrolyzate, and the like.

Examples of the dispersant include lignin sulfite waste liquor and methylcellulose.

Fixing agents can also be used in the formulations (powders, granules, emulsions), and examples of the fixing agent include carboxymethylcellulose, natural and synthetic polymers (for example, gum arabic, polyvinyl alcohol, polyvinyl acetate, and the like) and the like.

Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc.

The formulations in general can contain the active ingredient in an amount ranging from 0.1 to 95% by weight, and preferably 0.5 to 90% by weight.

The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100% by weight, and preferably 0.00001 to 1% by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil.

Next, the present invention is exemplified by way of the following examples, but the invention is not intended to be limited thereto.

TABLE 1

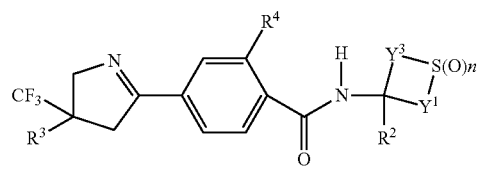

| | R³ | R⁴ | Y¹ | Y³ | R² | n |
|---|---|---|---|---|---|---|
| 1-1 | 3,4,5-trichloro-phenyl | Cl | CH2 | CH2 | H | 0 |
| 1-2 | 3,4,5-trichloro-phenyl | Cl | CH2 | CH2 | H | 1 |
| 1-3 | 3,4,5-trichloro-phenyl | Cl | CH2 | CH2 | H | 2 |
| 1-4 | 3,4,5-trichloro-phenyl | Br | CH2 | CH2 | H | 0 |
| 1-5 | 3,4,5-trichloro-phenyl | Br | CH2 | CH2 | H | 1 |
| 1-6 | 3,4,5-trichloro-phenyl | Br | CH2 | CH2 | H | 2 |
| 1-7 | 3,4,5-trichloro-phenyl | CF3 | CH2 | CH2 | H | 0 |
| 1-8 | 3,4,5-trichloro-phenyl | CF3 | CH2 | CH2 | H | 1 |
| 1-9 | 3,4,5-trichloro-phenyl | CF3 | CH2 | CH2 | H | 2 |
| 1-10 | 3,4,5-trichloro-phenyl | Me | CH2 | CH2 | H | 0 |
| 1-11 | 3,4,5-trichloro-phenyl | Me | CH2 | CH2 | H | 1 |
| 1-12 | 3,4,5-trichloro-phenyl | Me | CH2 | CH2 | H | 2 |
| 1-13 | 3,5-bis(trifluoromethyl)-phenyl | Cl | CH2 | CH2 | H | 0 |
| 1-14 | 3,5-bis(trifluoromethyl)-phenyl | Cl | CH2 | CH2 | H | 1 |
| 1-15 | 3,5-bis(trifluoromethyl)-phenyl | Cl | CH2 | CH2 | H | 2 |
| 1-16 | 3,5-bis(trifluoromethyl)-phenyl | CF3 | CH2 | CH2 | H | 0 |
| 1-17 | 3,5-bis(trifluoromethyl)-phenyl | CF3 | CH2 | CH2 | H | 1 |
| 1-18 | 3,5-bis(trifluoromethyl)-phenyl | CF3 | CH2 | CH2 | H | 2 |
| 1-19 | 3,5-bis(trifluoromethyl)-phenyl | Me | CH2 | CH2 | H | 0 |
| 1-20 | 3,5-bis(trifluoromethyl)-phenyl | Me | CH2 | CH2 | H | 1 |
| 1-21 | 3,5-bis(trifluoromethyl)-phenyl | Me | CH2 | CH2 | H | 2 |
| 1-22 | 3,4,5-trichloro-phenyl | F | CH2 | CH2 | H | 0 |
| 1-23 | 3,4,5-trichloro-phenyl | I | CH2 | CH2 | H | 0 |
| 1-24 | 3,5-bis(trifluoromethyl)-phenyl | F | CH2 | CH2 | H | 0 |
| 1-25 | 3,5-bis(trifluoromethyl)-phenyl | I | CH2 | CH2 | H | 0 |
| 1-26 | 3,4,5-trichloro-phenyl | Cl | C(Me)2 | CH2 | H | 0 |
| 1-27 | 3,5-bis(trifluoromethyl)-phenyl | Cl | C(Me)2 | CH2 | H | 0 |
| 1-28 | 3,4,5-trichloro-phenyl | Br | C(Me)2 | CH2 | H | 0 |
| 1-29 | 3,5-bis(trifluoromethyl)-phenyl | Br | C(Me)2 | CH2 | H | 0 |
| 1-30 | 3,4,5-trichloro-phenyl | CF3 | C(Me)2 | CH2 | H | 0 |
| 1-31 | 3,5-bis(trifluoromethyl)-phenyl | CF3 | C(Me)2 | CH2 | H | 0 |
| 1-32 | 3,4,5-trichloro-phenyl | Me | C(Me)2 | CH2 | H | 0 |
| 1-33 | 3,5-bis(trifluoromethyl)-phenyl | Me | C(Me)2 | CH2 | H | 0 |
| 1-34 | 3,4,5-trichloro-phenyl | Cl | C(Me)2 | C(Me)2 | H | 0 |
| 1-35 | 3,5-bis(trifluoromethyl)-phenyl | Cl | C(Me)2 | C(Me)2 | H | 0 |
| 1-36 | 3,4,5-trichloro-phenyl | Br | C(Me)2 | C(Me)2 | H | 0 |
| 1-37 | 3,5-bis(trifluoromethyl)-phenyl | Br | C(Me)2 | C(Me)2 | H | 0 |
| 1-38 | 3,4,5-trichloro-phenyl | CF3 | C(Me)2 | C(Me)2 | H | 0 |
| 1-39 | 3,5-bis(trifluoromethyl)-phenyl | CF3 | C(Me)2 | C(Me)2 | H | 0 |
| 1-40 | 3,4,5-trichloro-phenyl | Me | C(Me)2 | C(Me)2 | H | 0 |
| 1-41 | 3,5-bis(trifluoromethyl)-phenyl | Me | C(Me)2 | C(Me)2 | H | 0 |
| 1-42 | 3,4,5-trichloro-phenyl | Cl | C=O | CH2 | H | 0 |
| 1-43 | 3,5-bis(trifluoromethyl)-phenyl | Cl | C=O | CH2 | H | 0 |
| 1-44 | 3,4,5-trichloro-phenyl | Br | C=O | CH2 | H | 0 |
| 1-45 | 3,5-bis(trifluoromethyl)-phenyl | Br | C=O | CH2 | H | 0 |
| 1-46 | 3,4,5-trichloro-phenyl | CF3 | C=O | CH2 | H | 0 |
| 1-47 | 3,5-bis(trifluoromethyl)-phenyl | CF3 | C=O | CH2 | H | 0 |
| 1-48 | 3,4,5-trichloro-phenyl | Me | C=O | CH2 | H | 0 |
| 1-49 | 3,5-bis(trifluoromethyl)-phenyl | Me | C=O | CH2 | H | 0 |
| 1-50 | 3,5-dichloro-phenyl | Cl | CH2 | CH2 | H | 0 |
| 1-51 | 3,5-dichloro-phenyl | Br | CH2 | CH2 | H | 0 |
| 1-52 | 3,5-dichloro-phenyl | CF3 | CH2 | CH2 | H | 0 |
| 1-54 | 3-chloro-5-trifluoromethyl-phenyl | Cl | CH2 | CH2 | H | 0 |
| 1-55 | 3-chloro-5-trifluoromethyl-phenyl | Br | CH2 | CH2 | H | 0 |
| 1-56 | 3-chloro-5-trifluoromethyl-phenyl | CF3 | CH2 | CH2 | H | 0 |
| 1-57 | 3-chloro-5-trifluoromethyl-phenyl | Me | CH2 | CH2 | H | 0 |
| 1-58 | 3,5-dichloro-4-fluoro-phenyl | Cl | CH2 | CH2 | H | 0 |
| 1-59 | 3,5-dichloro-4-fluoro-phenyl | Br | CH2 | CH2 | H | 0 |
| 1-60 | 3,5-dichloro-4-fluoro-phenyl | CF3 | CH2 | CH2 | H | 0 |
| 1-61 | 3,5-dichloro-4-fluoro-phenyl | Me | CH2 | CH2 | H | 0 |
| 1-62 | 3,5-dibromo-phenyl | Cl | CH2 | CH2 | H | 0 |
| 1-63 | 3,5-dibromo-phenyl | Br | CH2 | CH2 | H | 0 |
| 1-64 | 3,5-dibromo-phenyl | CF3 | CH2 | CH2 | H | 0 |
| 1-65 | 3,5-dibromo-phenyl | Me | CH2 | CH2 | H | 0 |
| 1-66 | 3,4-dichloro-5-trifluoromethyl-phenyl | Cl | CH2 | CH2 | H | 0 |
| 1-67 | 3,4-dichloro-5-trifluoromethyl-phenyl | Br | CH2 | CH2 | H | 0 |
| 1-68 | 3,4-dichloro-5-trifluoromethyl-phenyl | CF3 | CH2 | CH2 | H | 0 |

TABLE 1-continued

| | R³ | R⁴ | Y¹ | Y³ | R² | n |
|---|---|---|---|---|---|---|
| 1-69 | 3,4-dichloro-5-trifluoromethyl-phenyl | Me | CH2 | CH2 | H | 0 |
| 1-70 | 2,6-dichloro-pyridin-4-yl | Cl | CH2 | CH2 | H | 0 |
| 1-71 | 2,6-dichloro-pyridin-4-yl | Br | CH2 | CH2 | H | 0 |
| 1-72 | 2,6-dichloro-pyridin-4-yl | CF3 | CH2 | CH2 | H | 0 |
| 1-73 | 2,6-dichloro-pyridin-4-yl | Me | CH2 | CH2 | H | 0 |
| 1-74 | 2,6-bis(trifluoromethyl)-pyridin-4-yl | Cl | CH2 | CH2 | H | 0 |
| 1-75 | 2,6-bis(trifluoromethyl)-pyridin-4-yl | Br | CH2 | CH2 | H | 0 |
| 1-76 | 2,6-bis(trifluoromethyl)-pyridin-4-yl | CF3 | CH2 | CH2 | H | 0 |
| 1-77 | 2,6-bis(trifluoromethyl)-pyridin-4-yl | Me | CH2 | CH2 | H | 0 |
| 1-78 | 3,4,5-trichloro-phenyl | Cl | CH2 | CH2 | Me | 0 |
| 1-79 | 3,5-bis(trifluoromethyl)-phenyl | Cl | CH2 | CH2 | Me | 0 |
| 1-80 | 3,4,5-trichloro-phenyl | Br | CH2 | CH2 | Me | 0 |
| 1-81 | 3,5-bis(trifluoromethyl)-phenyl | Br | CH2 | CH2 | Me | 0 |
| 1-82 | 3,4,5-trichloro-phenyl | CF3 | CH2 | CH2 | Me | 0 |
| 1-83 | 3,5-bis(trifluoromethyl)-phenyl | CF3 | CH2 | CH2 | Me | 0 |
| 1-84 | 3,4,5-trichloro-phenyl | Me | CH2 | CH2 | Me | 0 |
| 1-85 | 3,5-bis(trifluoromethyl)-phenyl | Me | CH2 | CH2 | Me | 0 |
| 1-86 | 3,4,5-trichloro-phenyl | NO2 | CH2 | CH2 | H | 0 |
| 1-87 | 3,4,5-trichloro-phenyl | SMe | CH2 | CH2 | H | 0 |
| 1-88 | 2,6-dichloro-pyridin-4-yl | Cl | CH2 | CH2 | H | 1 |
| 1-89 | 2,6-dichloro-pyridin-4-yl | Br | CH2 | CH2 | H | 1 |
| 1-90 | 2,6-dichloro-pyridin-4-yl | CF3 | CH2 | CH2 | H | 1 |
| 1-91 | 2,6-dichloro-pyridin-4-yl | Me | CH2 | CH2 | H | 1 |
| 1-92 | 2,6-bis(trifluoromethyl)-pyridin-4-yl | Cl | CH2 | CH2 | H | 1 |
| 1-93 | 2,6-bis(trifluoromethyl)-pyridin-4-yl | Br | CH2 | CH2 | H | 1 |
| 1-94 | 2,6-bis(trifluoromethyl)-pyridin-4-yl | CF3 | CH2 | CH2 | H | 1 |
| 1-95 | 2,6-bis(trifluoromethyl)-pyridin-4-yl | Me | CH2 | CH2 | H | 1 |
| 1-96 | 2,6-dichloro-pyridin-4-yl | Cl | CH2 | CH2 | H | 2 |
| 1-97 | 2,6-dichloro-pyridin-4-yl | Br | CH2 | CH2 | H | 2 |
| 1-98 | 2,6-dichloro-pyridin-4-yl | CF3 | CH2 | CH2 | H | 2 |
| 1-99 | 2,6-dichloro-pyridin-4-yl | Me | CH2 | CH2 | H | 2 |
| 1-100 | 2,6-bis(trifluoromethyl)-pyridin-4-yl | Cl | CH2 | CH2 | H | 2 |
| 1-101 | 2,6-bis(trifluoromethyl)-pyridin-4-yl | Br | CH2 | CH2 | H | 2 |
| 1-102 | 2,6-bis(trifluoromethyl)-pyridin-4-yl | CF3 | CH2 | CH2 | H | 2 |
| 1-103 | 2,6-bis(trifluoromethyl)-pyridin-4-yl | Me | CH2 | CH2 | H | 2 |
| 1-104 | 3,5-bis(trifluoromethyl)-phenyl | Br | CH2 | CH2 | H | 0 |
| 1-105 | 3,5-bis(trifluoromethyl)-phenyl | Br | CH2 | CH2 | H | 1 |
| 1-106 | 3,5-bis(trifluoromethyl)-phenyl | Br | CH2 | CH2 | H | 2 |

TABLE 2

| | R³ | R⁴ | Y¹ | Y³ | R² |
|---|---|---|---|---|---|
| 2-1 | 3,4,5-trichloro-phenyl | Cl | CH2 | CH2 | H |
| 2-2 | 3,5-bis(trifluoromethyl)-phenyl | Cl | CH2 | CH2 | H |
| 2-3 | 3,4,5-trichloro-phenyl | Br | CH2 | CH2 | H |
| 2-4 | 3,5-bis(trifluoromethyl)-phenyl | Br | CH2 | CH2 | H |
| 2-5 | 3,4,5-trichloro-phenyl | CF3 | CH2 | CH2 | H |
| 2-6 | 3,5-bis(trifluoromethyl)-phenyl | CF3 | CH2 | CH2 | H |
| 2-7 | 3,4,5-trichloro-phenyl | Me | CH2 | CH2 | H |
| 2-8 | 3,5-bis(trifluoromethyl)-phenyl | Me | CH2 | CH2 | H |
| 2-9 | 2,6-dichloro-pyridin-4-yl | Cl | CH2 | CH2 | H |
| 2-10 | 2,6-bis(trifluoromethyl)-pyridin-4-yl | Cl | CH2 | CH2 | H |
| 2-11 | 2,6-dichloro-pyridin-4-yl | Br | CH2 | CH2 | H |
| 2-12 | 2,6-bis(trifluoromethyl)-pyridin-4-yl | Br | CH2 | CH2 | H |
| 2-13 | 2,6-dichloro-pyridin-4-yl | CF3 | CH2 | CH2 | H |
| 2-14 | 2,6-bis(trifluoromethyl)-pyridin-4-yl | CF3 | CH2 | CH2 | H |
| 2-15 | 2,6-dichloro-pyridin-4-yl | Me | CH2 | CH2 | H |
| 2-16 | 2,6-bis(trifluoromethyl)-pyridin-4-yl | Me | CH2 | CH2 | H |
| 2-17 | 3,5-dichloro-phenyl | Cl | CH2 | CH2 | H |
| 2-18 | 3,5-dichloro-phenyl | Br | CH2 | CH2 | H |
| 2-19 | 3,5-dichloro-phenyl | CF3 | CH2 | CH2 | H |
| 2-20 | 3,5-dichloro-phenyl | Me | CH2 | CH2 | H |

TABLE 3

Structure: CF3-pyrrolidine(R3)-phenyl(R4)-C(O)NH-CH(Y)-C(O)-NH-thietane(Y3,Y1,R2,S(O)n)

| | R3 | R4 | Y | Y3 | R2 | n |
|---|---|---|---|---|---|---|
| 3-1 | 3,4,5-trichloro-phenyl | Cl | CH2 | CH2 | H | 0 |
| 3-2 | 3,4,5-trichloro-phenyl | Cl | CH2 | CH2 | H | 1 |
| 3-3 | 3,4,5-trichloro-phenyl | Cl | CH2 | CH2 | H | 2 |
| 3-4 | 3,4,5-trichloro-phenyl | Br | CH2 | CH2 | H | 0 |
| 3-5 | 3,4,5-trichloro-phenyl | Br | CH2 | CH2 | H | 1 |
| 3-6 | 3,4,5-trichloro-phenyl | Br | CH2 | CH2 | H | 2 |
| 3-7 | 3,4,5-trichloro-phenyl | CF3 | CH2 | CH2 | H | 0 |
| 3-8 | 3,4,5-trichloro-phenyl | CF3 | CH2 | CH2 | H | 1 |
| 3-9 | 3,4,5-trichloro-phenyl | CF3 | CH2 | CH2 | H | 2 |
| 3-10 | 3,4,5-trichloro-phenyl | Me | CH2 | CH2 | H | 0 |
| 3-11 | 3,4,5-trichloro-phenyl | Me | CH2 | CH2 | H | 1 |
| 3-12 | 3,4,5-trichloro-phenyl | Me | CH2 | CH2 | H | 2 |
| 3-13 | 3,5-bis(trifluoromethyl)-phenyl | Cl | CH2 | CH2 | H | 0 |
| 3-14 | 3,5-bis(trifluoromethyl)-phenyl | Cl | CH2 | CH2 | H | 1 |
| 3-15 | 3,5-bis(trifluoromethyl)-phenyl | Cl | CH2 | CH2 | H | 2 |
| 3-16 | 3,5-bis(trifluoromethyl)-phenyl | Br | CH2 | CH2 | H | 0 |
| 3-17 | 3,5-bis(trifluoromethyl)-phenyl | Br | CH2 | CH2 | H | 1 |
| 3-18 | 3,5-bis(trifluoromethyl)-phenyl | Br | CH2 | CH2 | H | 2 |
| 3-19 | 3,5-bis(trifluoromethyl)-phenyl | CF3 | CH2 | CH2 | H | 0 |
| 3-20 | 3,5-bis(trifluoromethyl)-phenyl | CF3 | CH2 | CH2 | H | 1 |
| 3-21 | 3,5-bis(trifluoromethyl)-phenyl | CF3 | CH2 | CH2 | H | 2 |
| 3-22 | 3,5-bis(trifluoromethyl)-phenyl | Me | CH2 | CH2 | H | 0 |
| 3-23 | 3,5-bis(trifluoromethyl)-phenyl | Me | CH2 | CH2 | H | 1 |
| 3-24 | 3,5-bis(trifluoromethyl)-phenyl | Me | CH2 | CH2 | H | 2 |
| 3-25 | 3,5-dichloro-phenyl | Cl | CH2 | CH2 | H | 0 |
| 3-26 | 3,5-dichloro-phenyl | Cl | CH2 | CH2 | H | 1 |
| 3-27 | 3,5-dichloro-phenyl | Cl | CH2 | CH2 | H | 2 |
| 3-28 | 3,5-dichloro-phenyl | Br | CH2 | CH2 | H | 0 |
| 3-29 | 3,5-dichloro-phenyl | Br | CH2 | CH2 | H | 1 |
| 3-30 | 3,5-dichloro-phenyl | Br | CH2 | CH2 | H | 2 |
| 3-31 | 3,5-dichloro-phenyl | CF3 | CH2 | CH2 | H | 0 |
| 3-32 | 3,5-dichloro-phenyl | CF3 | CH2 | CH2 | H | 1 |
| 3-33 | 3,5-dichloro-phenyl | CF3 | CH2 | CH2 | H | 2 |
| 3-34 | 3,5-dichloro-phenyl | Me | CH2 | CH2 | H | 0 |
| 3-35 | 3,5-dichloro-phenyl | Me | CH2 | CH2 | H | 1 |
| 3-36 | 3,5-dichloro-phenyl | Me | CH2 | CH2 | H | 2 |
| 3-37 | 2,6-dichloro-pyridin-4-yl | Cl | CH2 | CH2 | H | 0 |
| 3-38 | 2,6-dichloro-pyridin-4-yl | Cl | CH2 | CH2 | H | 1 |
| 3-39 | 2,6-dichloro-pyridin-4-yl | Cl | CH2 | CH2 | H | 2 |
| 3-40 | 2,6-dichloro-pyridin-4-yl | Br | CH2 | CH2 | H | 0 |
| 3-41 | 2,6-dichloro-pyridin-4-yl | Br | CH2 | CH2 | H | 1 |
| 3-42 | 2,6-dichloro-pyridin-4-yl | Br | CH2 | CH2 | H | 2 |
| 3-43 | 2,6-dichloro-pyridin-4-yl | CF3 | CH2 | CH2 | H | 0 |
| 3-44 | 2,6-dichloro-pyridin-4-yl | CF3 | CH2 | CH2 | H | 1 |
| 3-45 | 2,6-dichloro-pyridin-4-yl | CF3 | CH2 | CH2 | H | 2 |
| 3-46 | 2,6-dichloro-pyridin-4-yl | Me | CH2 | CH2 | H | 0 |
| 3-47 | 2,6-dichloro-pyridin-4-yl | Me | CH2 | CH2 | H | 1 |
| 3-48 | 2,6-dichloro-pyridin-4-yl | Me | CH2 | CH2 | H | 2 |
| 3-49 | 2,6-bis(trifluoromethyl)-pyridin-4-yl | Cl | CH2 | CH2 | H | 0 |
| 3-50 | 2,6-bis(trifluoromethyl)-pyridin-4-yl | Cl | CH2 | CH2 | H | 1 |
| 3-51 | 2,6-bis(trifluoromethyl)-pyridin-4-yl | Cl | CH2 | CH2 | H | 2 |
| 3-52 | 2,6-bis(trifluoromethyl)-pyridin-4-yl | Br | CH2 | CH2 | H | 0 |
| 3-53 | 2,6-bis(trifluoromethyl)-pyridin-4-yl | Br | CH2 | CH2 | H | 1 |
| 3-54 | 2,6-bis(trifluoromethyl)-pyridin-4-yl | Br | CH2 | CH2 | H | 2 |
| 3-55 | 2,6-bis(trifluoromethyl)-pyridin-4-yl | CF3 | CH2 | CH2 | H | 0 |
| 3-56 | 2,6-bis(trifluoromethyl)-pyridin-4-yl | CF3 | CH2 | CH2 | H | 1 |
| 3-57 | 2,6-bis(trifluoromethyl)-pyridin-4-yl | CF3 | CH2 | CH2 | H | 2 |
| 3-58 | 2,6-bis(trifluoromethyl)-pyridin-4-yl | Me | CH2 | CH2 | H | 0 |
| 3-59 | 2,6-bis(trifluoromethyl)-pyridin-4-yl | Me | CH2 | CH2 | H | 1 |
| 3-60 | 2,6-bis(trifluoromethyl)-pyridin-4-yl | Me | CH2 | CH2 | H | 2 |
| 3-61 | 3-chloro-5-trifluoromethyl-phenyl | Cl | CH2 | CH2 | H | 0 |
| 3-62 | 3-chloro-5-trifluoromethyl-phenyl | Br | CH2 | CH2 | H | 0 |
| 3-63 | 3-chloro-5-trifluoromethyl-phenyl | CF3 | CH2 | CH2 | H | 0 |
| 3-64 | 3-chloro-5-trifluoromethyl-phenyl | Me | CH2 | CH2 | H | 0 |
| 3-65 | 3,5-dichloro-4-fluoro-phenyl | Cl | CH2 | CH2 | H | 0 |
| 3-66 | 3,5-dichloro-4-fluoro-phenyl | Br | CH2 | CH2 | H | 0 |
| 3-67 | 3,5-dichloro-4-fluoro-phenyl | CF3 | CH2 | CH2 | H | 0 |
| 3-68 | 3,5-dichloro-4-fluoro-phenyl | Me | CH2 | CH2 | H | 0 |
| 3-69 | 3,5-dibromo-phenyl | Cl | CH2 | CH2 | H | 0 |
| 3-70 | 3,5-dibromo-phenyl | Br | CH2 | CH2 | H | 0 |
| 3-71 | 3,5-dibromo-phenyl | CF3 | CH2 | CH2 | H | 0 |
| 3-72 | 3,5-dibromo-phenyl | Me | CH2 | CH2 | H | 0 |
| 3-73 | 3,4-dichloro-5-trifluoromethyl-phenyl | Cl | CH2 | CH2 | H | 0 |
| 3-74 | 3,4-dichloro-5-trifluoromethyl-phenyl | Br | CH2 | CH2 | H | 0 |
| 3-75 | 3,4-dichloro-5-trifluoromethyl-phenyl | CF3 | CH2 | CH2 | H | 0 |
| 3-76 | 3,4-dichloro-5-trifluoromethyl-phenyl | Me | CH2 | CH2 | H | 0 |

TABLE 4

Structure: (CH3)3Si-CH2-N=C(SR10')-phenyl(R4)(T)

| | R4 | R10' | T |
|---|---|---|---|
| 3-1 | Me | H | CN |
| 3-2 | CF3 | H | CN |
| 3-3 | F | H | CN |
| 3-4 | Cl | H | CN |
| 3-5 | Br | H | CN |
| 3-6 | I | H | CN |
| 3-7 | SMe | H | CN |
| 3-8 | NO2 | H | CN |
| 3-9 | Me | Me | CN |
| 3-10 | CF3 | Me | CN |
| 3-11 | F | Me | CN |
| 3-12 | Cl | Me | CN |
| 3-13 | Br | Me | CN |
| 3-14 | I | Me | CN |
| 3-15 | SMe | Me | CN |
| 3-16 | NO2 | Me | CN |
| 3-17 | Me | H | CO2Me |
| 3-18 | CF3 | H | CO2Me |
| 3-19 | F | H | CO2Me |
| 3-20 | Cl | H | CO2Me |
| 3-21 | Br | H | CO2Me |
| 3-22 | I | H | CO2Me |
| 3-23 | Me | H | (thietan-3-yl)aminocarbonyl |
| 3-24 | CF3 | H | (thietan-3-yl)aminocarbonyl |
| 3-25 | F | H | (thietan-3-yl)aminocarbonyl |
| 3-26 | Cl | H | (thietan-3-yl)aminocarbonyl |
| 3-27 | Br | H | (thietan-3-yl)aminocarbonyl |
| 3-28 | I | H | (thietan-3-yl)aminocarbonyl |
| 3-29 | Me | H | (1-oxidothietan-3-yl)aminocarbonyl |
| 3-30 | CF3 | H | (1-oxidothietan-3-yl)aminocarbonyl |
| 3-31 | F | H | (1-oxidothietan-3-yl)aminocarbonyl |
| 3-32 | Cl | H | (1-oxidothietan-3-yl)aminocarbonyl |

TABLE 4-continued

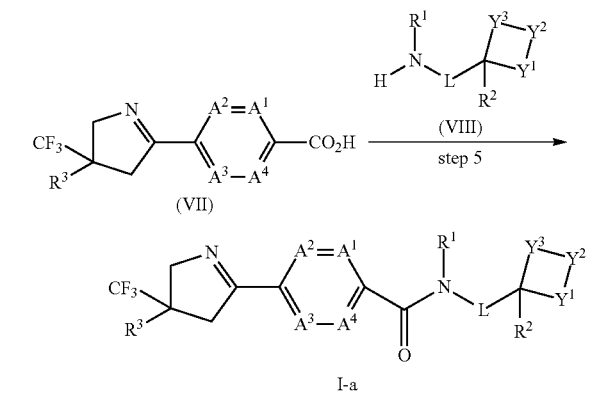

| | R⁴ | R¹⁰' | T |
|---|---|---|---|
| 3-33 | Br | H | (1-oxidothietan-3-yl)aminocarbonyl |
| 3-34 | I | H | (1-oxidothietan-3-yl)aminocarbonyl |
| 3-35 | Me | H | (1,1-dioxidothietan-3-yl)aminocarbonyl |
| 3-36 | CF3 | H | (1,1-dioxidothietan-3-yl)aminocarbonyl |
| 3-37 | F | H | (1,1-dioxidothietan-3-yl)aminocarbonyl |
| 3-38 | Cl | H | (1,1-dioxidothietan-3-yl)aminocarbonyl |
| 3-39 | Br | H | (1,1-dioxidothietan-3-yl)aminocarbonyl |
| 3-40 | I | H | (1,1-dioxidothietan-3-yl)aminocarbonyl |

Compounds according to the invention can be prepared by known methods with known starting materials, and for example by following one of the following reaction schemes.

Reaction scheme 1:

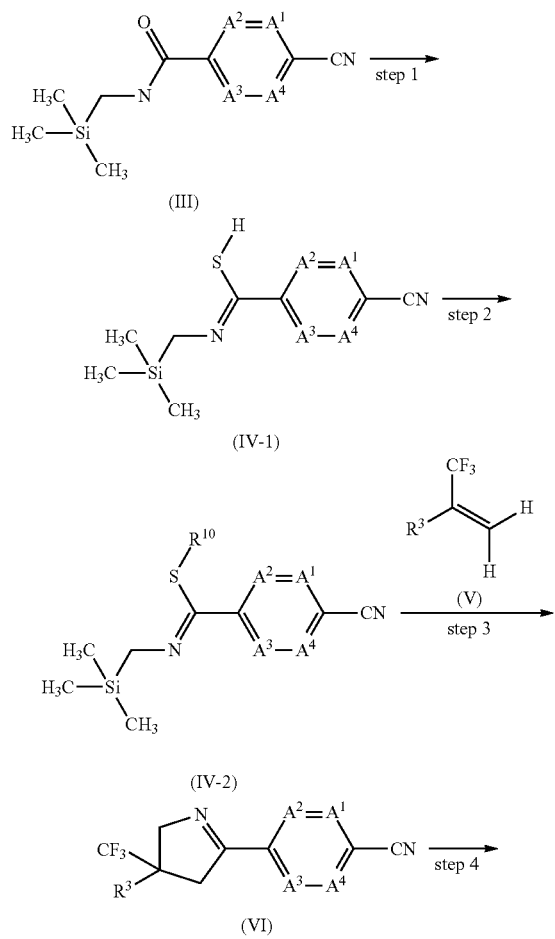

Wherein L, $R^1$, $R^2$, $R^4$, $Y^1$, $Y^2$, $Y^3$, $A^1$, $A^2$, $A^3$, and $A^4$ are as defined herein; and $R^{10'}$ stands for $C_1$-$C_8$alkyl, preferably methyl.

The cyclization from compounds of formula (IV-1) to compounds of formula (VI) is described in WO2009/097992. Further reaction of compound (VI) to yield compounds of formula (1-a) can be done using generally known methods.

Reaction scheme 2

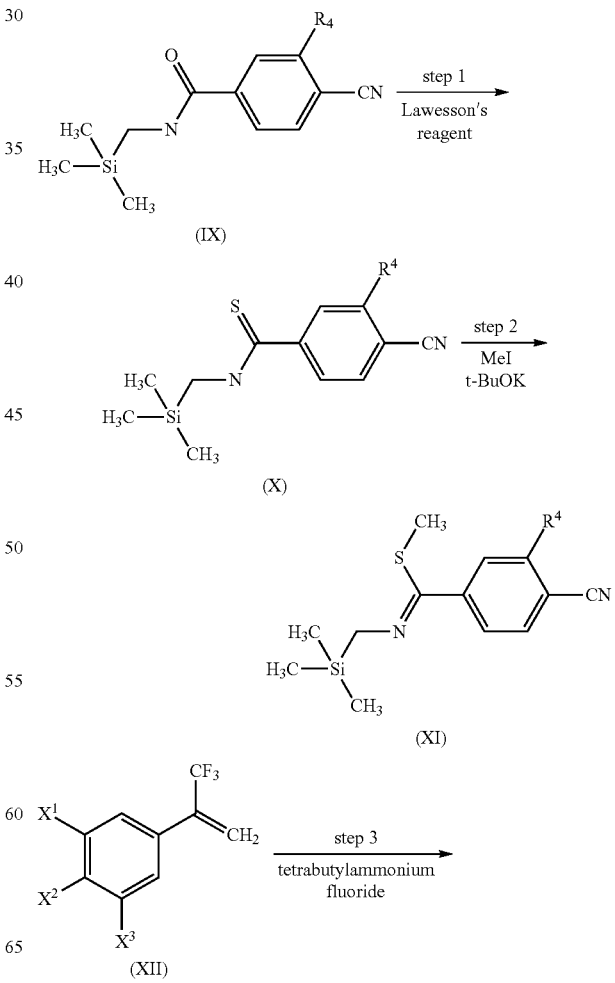

-continued

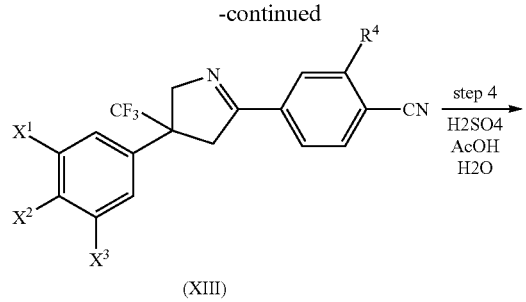

(XIII)

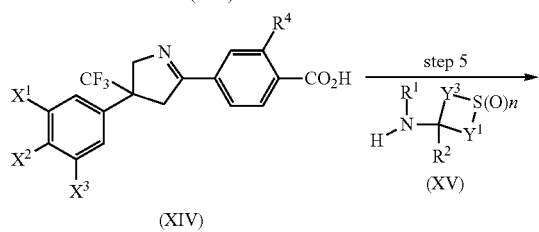

(XIV)

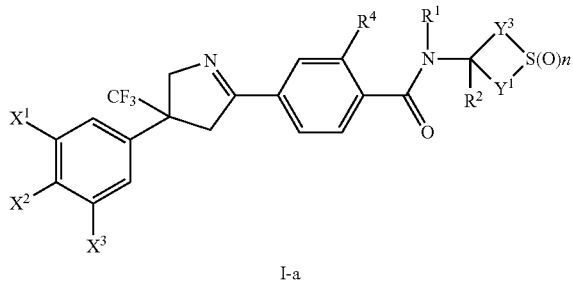

I-a

Compounds of formula (XIII) can be synthesized according to the synthetic method in WO09/097,992, and can be hydrolyzed using generally known methods to give compounds of formula (XIV). Compounds of formula (1-a) can be synthesized by amidation reaction of compounds of formula (XIV) with compounds of formula (XV) using a condensation reagent like e.g. 1-ethyl-3-(3-dimethylaminopropyl)-carbodiimide.

A useful Lawesson's reagent is 2,4-bis(4-methoxyphenyl)-1,3-dithia-2,4-diphosphetane-2,4-disulfide.

Reaction scheme 3:

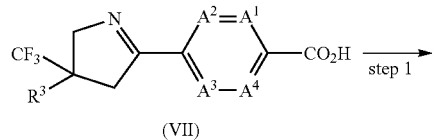

(VII)

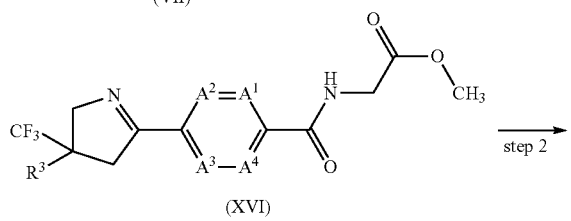

(XVI)

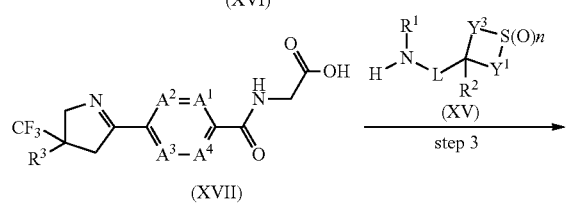

(XVII)

-continued

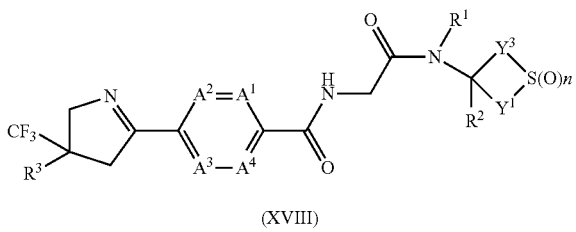

(XVIII)

Compounds of formula (XVI) can be synthesized using a condensation reagent like e.g. 1-ethyl-3-(3-dimethylaminopropyl)-carbodiimide, and can be hydrolyzed using generally known methods to give compounds of formula (XVII). Compounds of formula (XVIII) can be synthesized by amidation reaction of compounds of formula (XVII) with compounds of formula (XV) using a condensation reagent like e.g. 1-ethyl-3-(3-dimethylaminopropyl)-carbodiimide.

Compounds of the formula (IX) can be synthesized according to the method shown in the reaction scheme 4 or in the reaction scheme 5.

Reaction scheme 4:

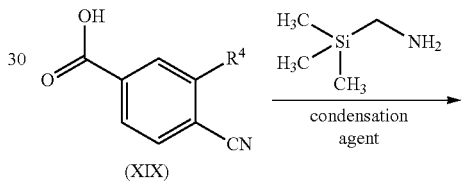

(XIX)

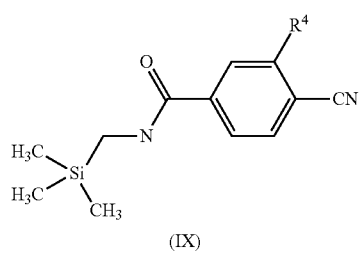

(IX)

Reaction scheme 5:

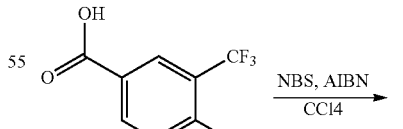

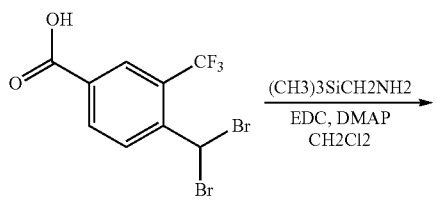

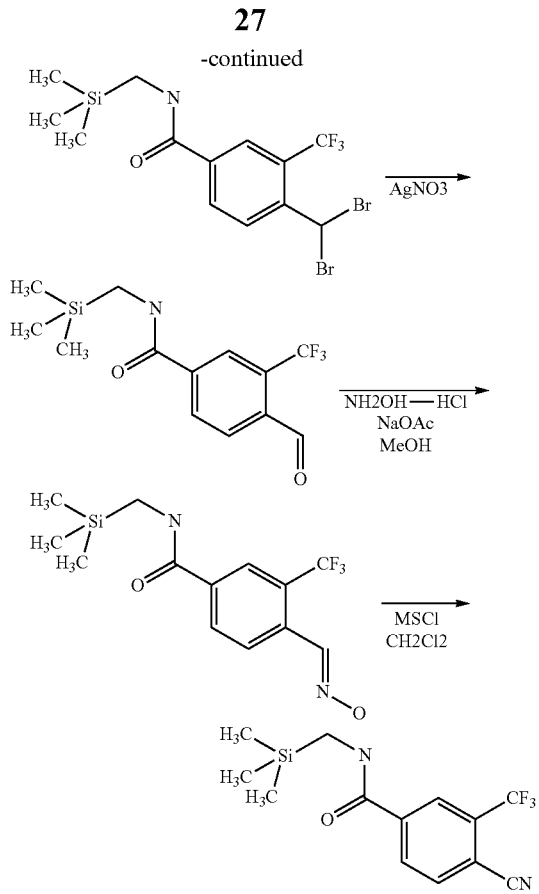

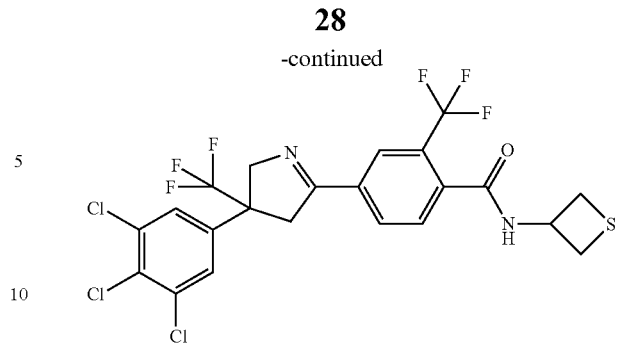

To the solution of thietan-3-amine hydrobromide (40 mg, 0.23 mmol) in 1,2-dichloromethane was added triethylamine (60 mg, 0.59 mmol) at 0° C. After that 1-(3-Dimethylaminopropyl)-3-ethylcarbodiimide hydrochloride (54 mg, 0.23 mmol), 1-hydroxybenzotriazole monohydrate (32 mg, 0.23 mmol), and 4-[3-(3,4,5-trichlorophenyl)-3-(trifluoromethyl)-3,4-dihydro-2H-pyrrol-5-yl]-2-(trifluoromethyl)benzoic acid (100 mg, 0.19 mmol) were added to the solution at 0° C. Then the reaction mixture was stirred overnight at room temperature and diluted with t-butylmethylether, and washed with water, and dried over magnesium sulfate anhydrous. After evaporation, the residue was purified with silicagel column chromatography to give 75 mg of N-(thietan-3-yl)-4-[3-(3,4,5-trichlorophenyl)-3-(trifluoromethyl)-3,4-dihydro-2H-pyrrol-5-yl]-2-(trifluoromethyl)benzamide.

1H-NMR (CDCl$_3$) δ: 3.36-3.50 (5H, m), 3.81 (1H, dd), 4.47 (1H, d), 4.93 (1H, dd), 5.34-5.48 (1H, m), 6.34 (1H, br d), 7.41 (2H, s), 7.61 (1H, d), 8.05 (1H, dd), 8.18 (1H, s).

Synthesis of 2-methyl-N-(thietan-3-yl)-4-[3-(3,4,5-trichlorophenyl)-3-(trifluoromethyl)-3,4-dihydro-2H-pyrrol-5-yl]benzamide (compound 1-10)

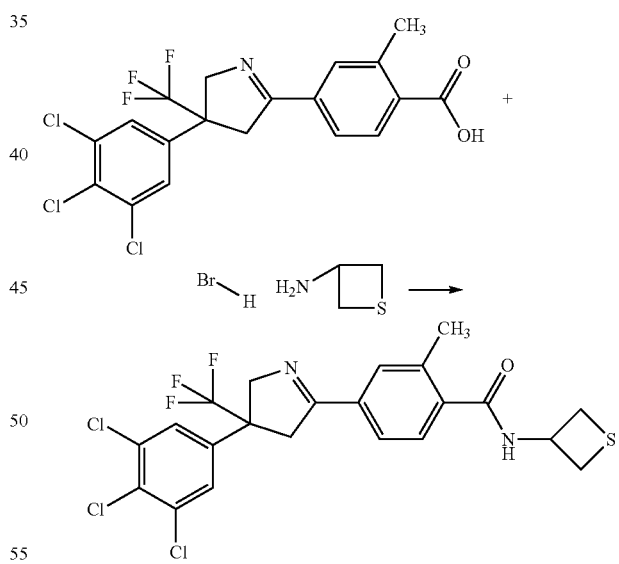

To a solution of thietan-3-amine hydrobromide in N,N-dimethylformamide, triethylamine was added at 0° C. Then 1-(3-Dimethylaminopropyl)-3-ethylcarbodiimide hydrochloride (122 mg, 0.53 mmol), 1-hydroxybenzotriazole monohydrate (72 mg, 0.53 mmol), and 2-methyl-4-[3-(3,4,5-trichlorophenyl)-3-(trifluoromethyl)-3,4-dihydro-2H-pyrrol-5-yl]benzoic acid (200 mg, 0.44 mmol) were added to the solution. The reaction mixture was stirred overnight at room temperature and then diluted with t-BuOMe and washed with 2M HCl, and after that with H$_2$O, saturated NaCl aq. and dried over MgSO$_4$. After evaporation, the residue was purified with chromatography (220 mg, 95%).

In this scheme NBS stands for N-bromosuccinimide, AIBN stands for azobisisobutyronitrile, EDC stands for 1-ethyl-3-(3-dimethylaminopropyl)-carbodiimide, DMAP stands for 4-(dimethylamino)pyridine, MsCl stands for methanesulfonyl chloride.

4-Cyano-3-methylbenzolic acid was prepared according to the synthetic method described in Bioorganic & Medicinal Chemistry Letters 14(17) 4585-4589 (2004).

SYNTHESIS EXAMPLES

Synthesis of N-(thietan-3-yl)-4-[3-(3,4,5-trichlorophenyl)-3-(trifluoromethyl)-3,4-dihydro-2H-pyrrol-5-yl]-2-(trifluoromethyl)benzamide (compound 1-7)

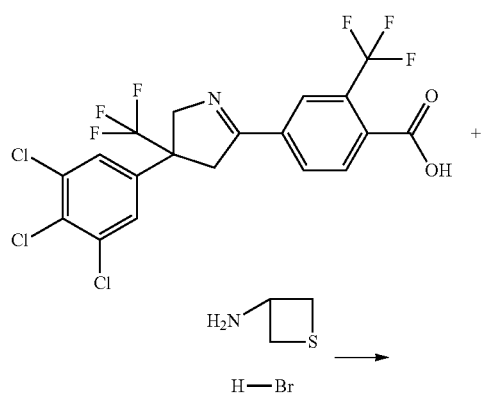

1H-NMR (CDCl₃) δ: 2.49 (3H, s), 3.36-3.53 (6H, m), 3.79 (1H, dd), 4.44 (1H, d), 4.89 (1H, dd), 5.36-5.50 (1H, m), 6.23 (1H, br d), 7.44-7.41 (3H, m), 7.67-7.72 (2H, m).

The following compounds were prepared analogously to beforementioned methods.

4-{3-[3,5-Bis(trifluoromethyl)phenyl}-3-(trifluoromethyl)-3,4-dihydro-2H-pyrrol-5-yl]-N-(thietan-3-yl)-2-(trifluoromethyl)benzamide (compound 1-16)

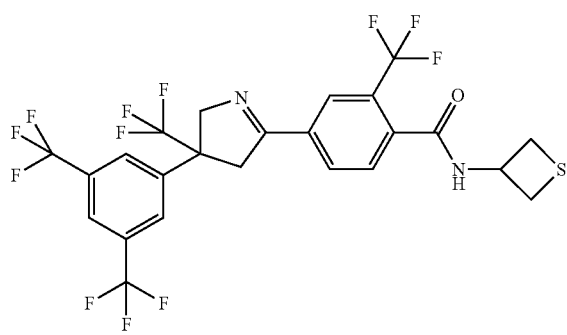

1H-NMR (CDCl₃) δ: 3.36-3.57 (5H, m), 3.93 (1H, dd), 4.55 (1H, d), 5.06 (1H, dd), 5.48-5.34 (1H, m), 6.36 (1H, d), 7.62 (1H, d), 7.83 (2H, s), 7.93 (1H, s), 8.08 (1H, d), 8.20 (1H, s).

4-{3-[3,5-Bis(trifluoromethyl)phenyl]-3-(trifluoromethyl)-3,4-dihydro-2H-pyrrol-5-yl}-2-methyl-N-(thietan-3-yl)benzamide (compound 1-19)

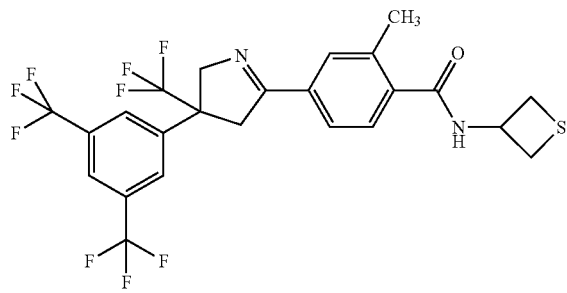

1H-NMR (CDCl₃) δ: 2.44 (3H, s), 3.41 (4H, d), 3.53 (1H, d), 3.92 (1H, dd), 4.50 (1H, d), 5.00 (1H, dd), 5.30-5.44 (1H, m), 6.86 (1H, br t), 7.39 (1H, d), 7.65-7.70 (2H, m), 7.84 (2H, s), 7.92 (1H, s).

2-Bromo-N-(thietan-3-yl)-4-[3-(3,4,5-trichlorophenyl)-3-(trifluoromethyl)-3,4-dihydro-2H-pyrrol-5-yl]benzamide (compound 1-4)

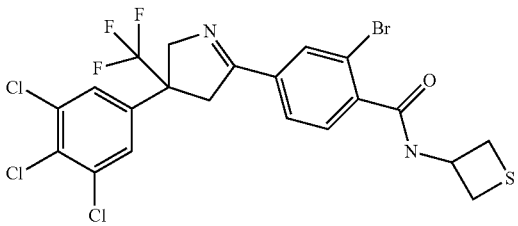

1H-NMR (CDCl₃) δ: 3.40-3.52 (5H, m), 3.76 (1H, dd), 4.45 (1H, d), 4.91 (1H, dd), 5.37-5.50 (1H, m), 6.58 (1H, br d), 7.39 (2H, s), 7.61 (1H, d, J=8.1 Hz), 7.81 (1H, dd), 8.08 (1H, d).

4-{3-[3,5-Bis(trifluoromethyl)phenyl]-3-(trifluoromethyl)-3,4-dihydro-2H-pyrrol-5-yl}-2-bromo-N-(thietan-3-yl) benzamide (compound 1-104)

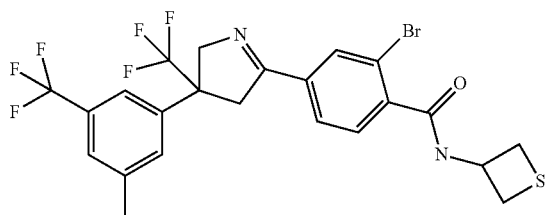

1H-NMR (CDCl₃) δ: 3.41-3.52 (5H, m), 3.88 (1H, dd), 4.53 (1H, d), 5.04 (1H, dd), 5.37-5.51 (1H, m), 6.52 (1H, br d), 7.63 (1H, d), 7.86-7.81 (3H, m), 7.92 (1H, s), 8.12 (1H, s).

Synthesis of N-(1,1-dioxidothietan-3-yl)-2-methyl-4-[3-(3,4,5-trichlorophenyl)-3-(trifluoromethyl)-3,4-dihydro-2H-pyrrol-5-yl]benzamide (compound 1-12) and 2-methyl-N-(1-oxidothietan-3-yl)-4-[3-(3,4,5-trichlorophenyl)-3-(trifluoromethyl)-3,4-dihydro-2 pyrrol-5-yl]benzamide (compound 1-11)

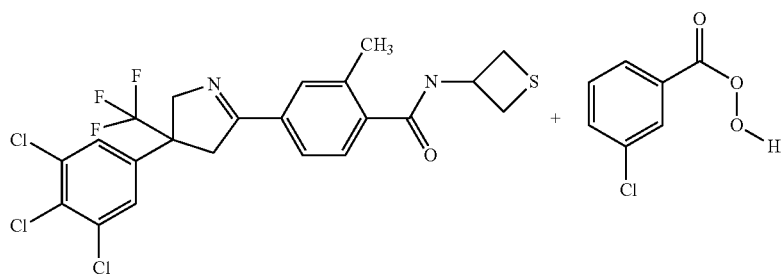

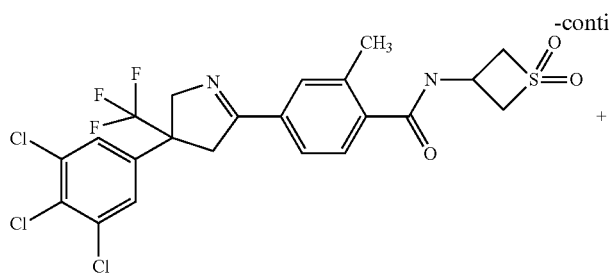
+
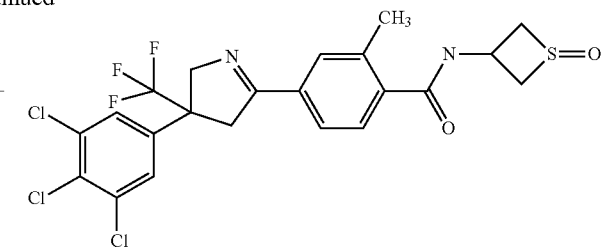

2-Methyl-N-(thietan-3-yl)-4-[3-(3,4,5-trichlorophenyl)-3-(trifluoromethyl)-3,4-dihydro-2H-pyrrol-5-yl]-benzamide (300 mg, 0.57 mmol) was dissolved in $CH_2Cl_2$ and stirred at 0° C. To the solution was added saturated aqueous sodium hydrogen carbonate and 3-chloroperbenzoic acid (229 mg, 0.86 mmol) at 0° C. Reaction mixture was stirred overnight at room temperature. The reaction mixture was evaporated and purified with column chromatography to give N-(1,1-dioxidothietan-3-yl)-2-methyl-4-[3-(3,4,5-tri-chlorophenyl)-3-(trifluoromethyl)-3,4-dihydro-2H-pyrrol-5-yl]benzamide (210 mg, 66%) and 2-methyl-N-(1-oxidothietan-3-yl)-4-[3-(3,4,5-trichlorophenyl)-3-(trifluoromethyl)-3,4-dihydro-2H-pyrrol-5-yl]benzamide (83 mg, 27%).

N-(1,1-Dioxidothietan-3-yl)-2-methyl-4-[3-(3,4,5-trichlorophenyl)-3-(trifluoromethyl)-3,4-dihydro-2H-pyrrol-5-yl]benzamide (compound 1-12): 1H-NMR ($CDCl_3$) δ: 2.48 (3H, s), 3.44 (1H, d), 3.79 (1H, dd), 4.02-4.08 (2H, m), 4.43 (1H, d), 4.56-4.64 (2H, m), 4.81-4.92 (2H, m), 6.76 (1H, br d), 7.41-7.46 (3H, m), 7.66-7.72 (2H, m).

2-Methyl-N-(1-oxidothietan-3-yl)-4-[3-(3,4,5-trichlorophenyl)-3-(trifluoromethyl)-3,4-dihydro-2H-pyrrol-5-yl]benzamide (compound 1-11): 1H-NMR ($CDCl_3$) δ: 2.48 (3H, s), 3.26-3.34 (2H, m), 3.44 (1H, d), 3.79 (1H, dd), 4.14-4.20 (2H, m), 4.41 (1H, d), 4.61-4.73 (1H, m), 4.86 (1H, dd), 6.86 (1H, br d), 7.45-7.40 (3H, m), 7.71-7.66 (2H, m).

The following compounds were prepared analogously to before mentioned methods.

4-{3-[3,5-Bis(trifluoromethyl)phenyl]-3-(trifluoromethyl)-3,4-dihydro-2H-pyrrol-5-yl}-N-(1,1-dioxidothietan-3-yl)-2-methylbenzamide (compound 1-21)

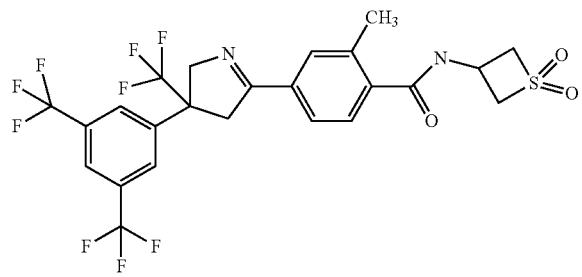

1H-NMR ($CDCl_3$) δ: 2.49 (3H, s), 3.51 (1H, d), 3.91 (1H, dd), 4.02-4.08 (2H, m), 4.48-4.64 (3H, m), 4.82-4.92 (1H, m), 5.01 (1H, dd), 6.76 (1H, d), 7.45 (1H, d), 7.74-7.69 (2H, m), 7.83 (2H, s), 7.92 (1H, s).

4-{3-[3,5-Bis(trifluoromethyl)phenyl]-3-(trifluoromethyl)-3,4-dihydro-2H-pyrrol-5-yl}-2-methyl-N-(1-oxidothietan-3-yl)benzamide (compound 1-20)

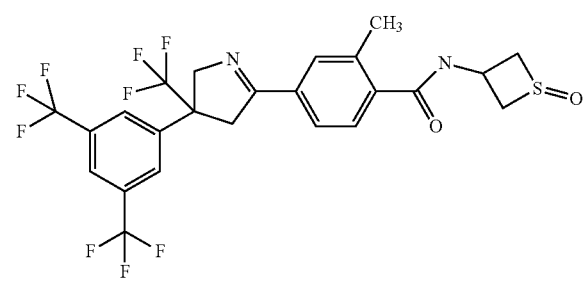

1H-NMR ($CDCl_3$) δ: 2.48 (3H, s), 3.28-3.36 (2H, m), 3.51 (1H, d), 3.91 (1H, d), 4.13-4.20 (2H, m), 4.48 (1H, d), 4.62-4.76 (1H, m), 4.98 (1H, d), 7.01 (1H, br s), 7.45 (1H, d), 7.69-7.92 (5H, m).

N-(1,1-Dioxidothietan-3-yl)-4-[3-(3,4,5-trichlorophenyl)-3-(trifluoromethyl)-3,4-dihydro-2H-pyrrol-5-yl]-2-(trifluoromethyl)benzamide (compound 1-9)

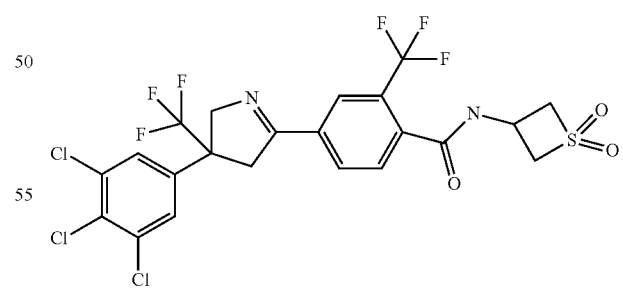

1H-NMR ($CDCl_3$) δ: 3.48 (1H, d), 3.81 (1H, dd), 4.01-4.07 (2H, m), 4.45-4.63 (3H, m), 4.83-4.97 (2H, m), 6.94 (1H, br d), 7.41 (2H, s), 7.59 (1H, d), 8.05 (1H, dd, J=7.9, 0.9 Hz), 8.17 (1H, s).

N-(1-Oxidothietan-3-yl)-4-[3-(3,4,5-trichlorophenyl)-3-(trifluoromethyl)-3,4-dihydro-2H-pyrrol-5-yl]-2-(trifluoromethyl)benzamide (compound 1-8)

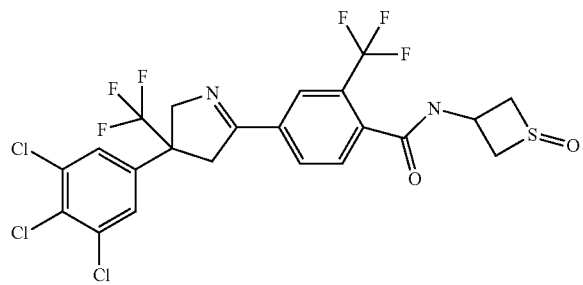

1H-NMR (CDCl₃) δ: 3.27-3.34 (2H, m), 3.47 (1H, d), 3.81 (1H, d), 4.11-4.18 (2H, m), 4.46 (1H, d), 4.58-4.74 (1H, m), 4.92 (1H, d), 7.23 (1H, br d), 7.41 (2H, s), 7.56 (1H, d), 8.03 (1H, d), 8.15 (1H, s).

Synthesis of Methyl N-{4-[3-(3,4,5-trichlorophenyl)-3-(trifluoromethyl)-3,4-dihydro-2H-pyrrol-5-yl]-2-(trifluoromethyl)-benzoyl}glycinate

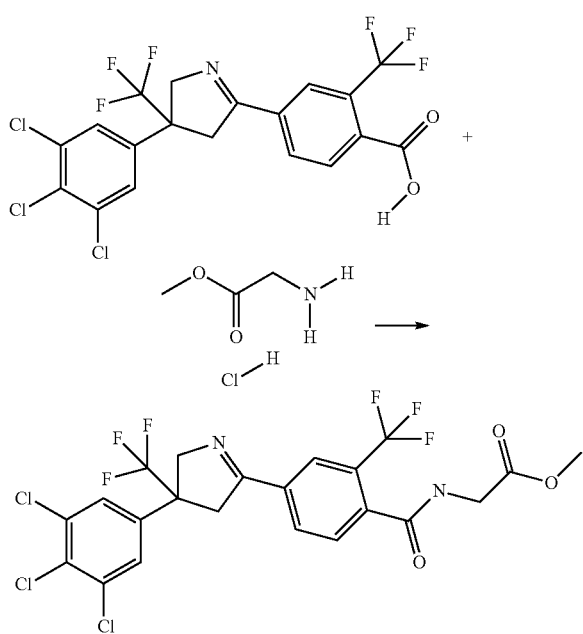

To the solution of methyl glycinate hydrochloride (0.36 g, 2.89 mmol) in N,N-dimethylformamide was added triethylamine (0.59 g, 5.78 mmol) at 0° C. Then 1-(3-dimethylaminopropyl)-3-ethyl carbodiimide hydrochloride (0.40 g, 1.73 mmol), 4-[3-(3,4,5-trichlorophenyl)-3-(trifluoromethyl)-3,4-dihydro-2H-pyrrol-5-yl]-2-(trifluoromethyl)benzoic acid (0.73 g, 1.44 mmol) was added to the solution. Reaction mixture was stirred for overnight at room temperature. The reaction mixture was diluted with t-BuOMe, washed with H₂O, and dried over MgSO₄. After evaporation, the residue was purified by column chromatography (0.13 g, 16%).

1H-NMR (CDCl₃) δ: 3.49 (1H, d), 3.78-3.84 (4H, m), 4.24 (2H, d), 4.47 (1H, d), 4.93 (1H, dd), 6.66-6.72 (1H, m), 7.41 (2H, s), 7.63 (1H, d), 8.01 (1H, d), 8.15 (1H, s).

Methyl N-[4-{3-[3,5-bis(trifluoromethyl)phenyl]-3-(trifluoromethyl)-3,4-dihydro-2H-pyrrol-5-yl}-2-(trifluoromethyl)benzoyl]glycinate was synthesized by the same method

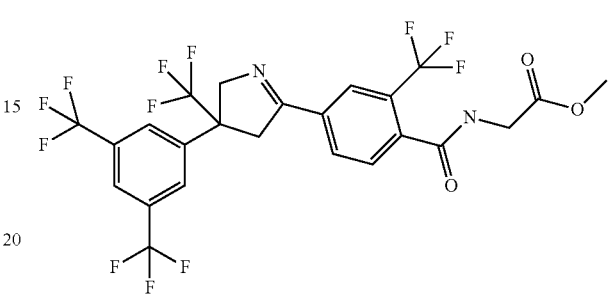

1H-NMR (CDCl₃) δ: 3.55 (1H, d), 3.82 (3H, s), 3.93 (1H, dd), 4.26 (2H, d), 4.55 (1H, d), 5.06 (1H, dd), 6.44 (1H, t), 7.69 (1H, d), 7.83 (2H, s), 7.93 (1H, s), 8.09 (1H, d), 8.22 (1H, s).

Synthesis of N-[4-{3-[3,5-bis(trifluoromethyl)phenyl]-3-(trifluoromethyl)-3,4-dihydro-2H-pyrrol-5-yl}-2-(trifluoromethyl)benzoyl]glycine

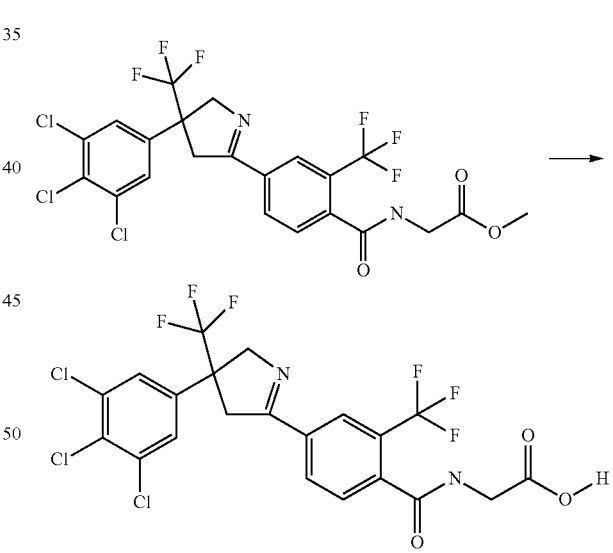

Sodium hydroxide (22 mg, 0.50 mmol) was added to Methyl N-{4-[3-(3,4,5-trichlorophenyl)-3-(trifluoromethyl)-3,4-dihydro-2H-pyrrol-5-yl]-2-(trifluoromethyl)benzoyl}glycinate (130 mg, 0.22 mmol) in Water (1 ml) and EtOH (5 ml), and stirred at ambient temperature for overnight. 2NHCl was added into the mixture, and extracted with t-BuOMe three times, and dried over MgSO4. After evaporated, the crude product was got (120.0 mg, 94%).

1H-NMR (CDCl₃) δ: 3.52 (1H, d), 3.81 (1H, d), 4.17 (2H, d), 4.46 (1H, d), 4.90 (1H, d), 7.06 (1H, t), 7.39 (3H, s), 7.60 (1H, d), 7.98 (1H, d), 8.08 (1H, s).

N-[4-{3-[3,5-Bis(trifluoromethyl)phenyl]-3-(trifluoromethyl)-3,4-dihydro-2H-pyrrol-5-yl}-2-(trifluoromethyl)benzoyl]glycine was synthesized by the same method

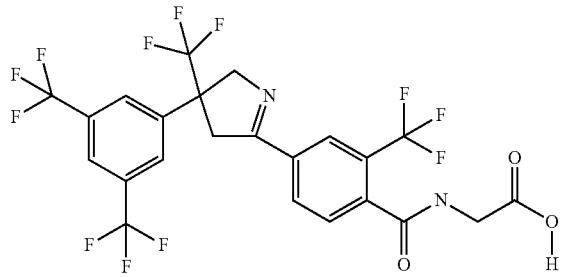

1H-NMR (CDCl₃) δ: 3.55 (1H, d), 3.94 (1H, d), 4.30 (2H, d), 4.56 (1H, d), 5.06 (1H, d), 6.41 (1H, br s), 7.70 (1H, d), 7.83 (2H, s), 7.93 (1H, s), 8.09 (1H, d), 8.22 (1H, s).

Synthesis of N-[2-oxo-2-(thietan-3-ylamino)ethyl]-4-[3-(3,4,5-trichlorophenyl)-3-(trifluoromethyl)-3,4-dihydro-2H-pyrrol-5-yl]2-trifluoromethyl)benzamide (Compound No. 3-7)

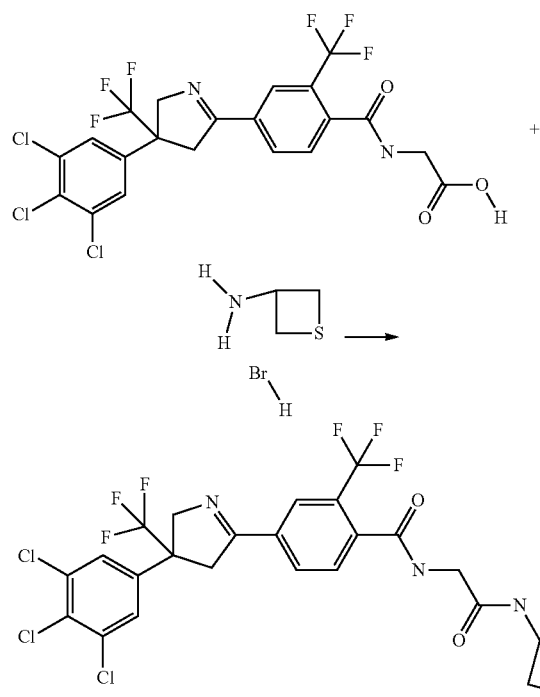

To the solution of thietan-3-amine hydrobromide (29 mg, 0.13 mmol) in N,N-Dimethylformamide was added triethylamine at 0° C. Then 1-(3-Dimethylaminopropyl)-3-ethylcarbodiimide hydrochloride (39 mg, 0.17 mmol), 1-hydroxybenzotriazole monohydrate (23 mg, 0.17 mmol), N-[4-{3-[3,5-bis(trifluoromethyl)phenyl]-3-(trifluoromethyl)-3,4-dihydro-2H-pyrrol-5-yl}-2-(trifluoromethyl)benzoyl]glycine (80 mg, 0.14 mmol) were added to the solution. Reaction mixture was stirred for overnight at room temperature. The reaction mixture was diluted with t-BuOMe, washed with 2M HCl, then H₂O, then saturated NaCl aq. and dried over MgSO₄. After evaporation, the residue was purified with chromatography (60 mg, 66%).

1H-NMR (CD3OD) δ: 3.23-3.29 (2H, m), 3.40-3.46 (2H, m), 3.75 (1H, d), 3.95-4.01 (3H, m), 4.51 (1H, d), 4.92 (1H, d), 5.11-5.23 (1H, m), 7.68 (2H, s), 7.79 (1H, d), 8.18 (1H, dd), 8.31 (1H, s).

4-{3-[3,5-Bis(trifluoromethyl)phenyl]-3-(trifluoromethyl)-3,4-dihydro-2H-pyrrol-5-yl}-N-[2-oxo-2-(thietan-3-ylamino)ethyl]-2-(trifluoromethyl)benzamide (Compound No. 3-19) was synthesized by the same method

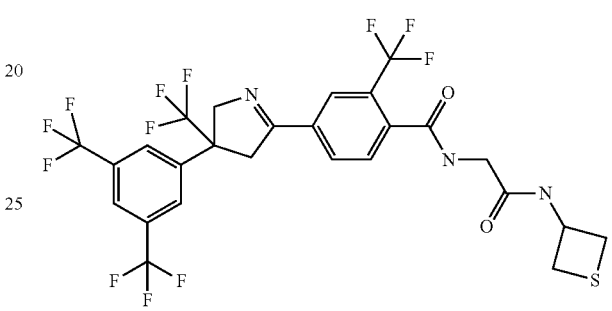

1H-NMR (CDCl₃) δ: 3.07-3.24 (4H, m), 3.47 (1H, d), 3.84-3.78 (3H, m), 4.36 (1H, d), 4.85 (1H, dd), 4.94-5.05 (1H, m), 7.51 (1H, d), 7.69 (2H, s), 7.74 (1H, s), 7.92 (1H, d), 8.06 (1H, s).

Synthesis of 4-(dibromomethyl)-3-(trifluoromethyl)benzoic acid

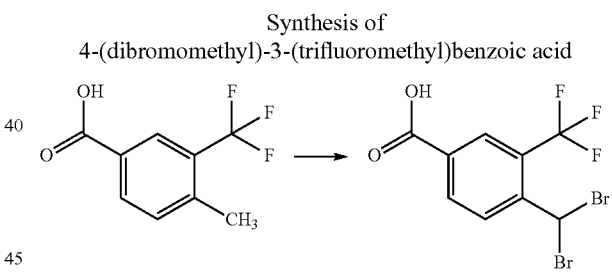

4-Methyl-3-(trifluoromethyl)benzoic acid (10 g, 48.8 mmol) and N-Bromosuccinimide (20 g, 112 mmol) in CCl₄ were refluxed for 1 hour by using UV lamp. Filtrated by using a celite pad and evaporated. The residue was diluted with t-BuOMe, washed with H₂O and dried over MgSO₄. After evaporation the product was found to be 18.0 g (100%).

1H-NMR (CDCl₃) δ: 7.03 (1H, s), 8.40-8.32 (3H, m).

Synthesis of 4-(dibromomethyl)-3-(trifluoromethyl)-N-[(trimethylsilyl)methyl]benzamide

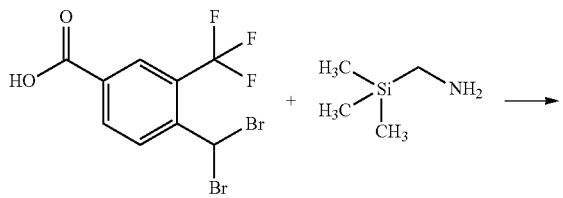

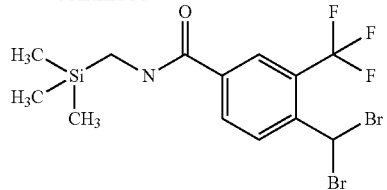

4-(dibromomethyl)-3-(trifluoromethyl)benzoic acid (18.0 g, 49.7 mmol) was suspended in CH$_2$Cl$_2$. 1-(Trimethylsilyl)methanamine (5.1 g, 49.7 mmol) and 1-(3-Dimethylaminopropyl)-3-ethylcarbodiimide hydrochloride (12.5 g, 54.7 mmol) were added to the solution at 0° C. The reaction mixture was stirred at room temperature over night. The reaction mixture was diluted with t-BuOMe and washed with 2M HCl, H$_2$O, and brine. After drying over MgSO$_4$ and evaporation, the product was found to be 22.0 g (99%).

1H-NMR (CDCl3) δ: 0.13 (9H, s), 2.98 (2H, d), 6.17 (1H, br s), 7.01 (1H, s), 7.95-7.99 (2H, m), 8.25 (1H, d).

4-Cyano-3-methyl-N-[(trimethylsilyl)methyl]benzamide was synthesized by the same method

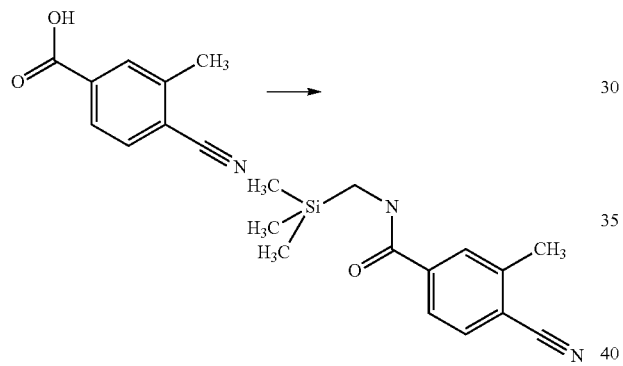

1H-NMR (CDCl3) δ: 2.61 (3H, s), 3.95 (2H, s), 7.68 (1H, d), 7.93 (1H, dd), 7.99 (1H, d).

Synthesis of 4-formyl-3-(trifluoromethyl)-N-[(trimethylsilyl)methyl]benzamide

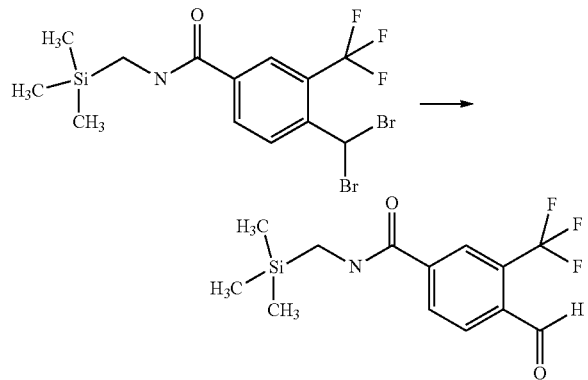

4-(dibromomethyl)-3-(trifluoromethyl)-N-[(trimethylsilyl)methyl]benzamide (22.0 g, 49.1 mmol) and AgNO$_3$ (16.7 g, 98.3 mmol) in EtOH and H$_2$O were refluxed for 2 hours, then diluted with t-BuOMe and washed with brine. Dried over MgSO$_4$ and evaporation yielded the product (15.0 g, 100%).

1H-NMR (CDCl3) δ: 0.15 (9H, s), 3.01 (2H, d), 6.49 (1H, br s), 8.01 (1H, d), 8.15-8.17 (2H, m), 10.40 (1H, d).

Synthesis of 4-[(E)-(hydroxyimino)methyl]-3-(trifluoromethyl)-N-[(trimethylsilyl)methyl]benzamide

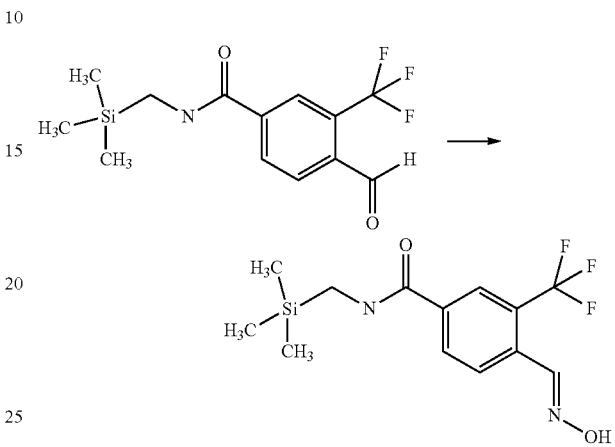

4-Formyl-3-(trifluoromethyl)-N-[(trimethylsilyl)methyl]benzamide (15.0 g, 49.4 mmol), Hydroxylamine hydrochloride (6.9 g, 98.8 mmol) and sodium acetate (6.1 g, 74.1 mmol) in EtOH and H$_2$O were stirred at room temperature over night. The reaction mixture was diluted with t-BuOMe, and washed with brine and dried over MgSO$_4$. After evaporation the product was found to be 15.0 g (95%).

1H-NMR (CDCl3) δ: 0.14 (9H, s), 3.00 (2H, d), 6.21 (1H, br s), 7.87 (1H, d), 8.04-8.05 (2H, m), 8.49 (1H, d).

Synthesis of 4-cyano-3-(trifluoromethyl)-N-[(trimethylsilyl)methyl]benzamide

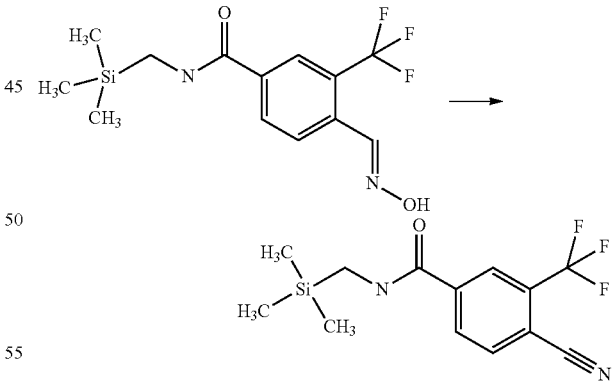

Methanesulfonyl chloride (5.6 g, 49.0 mmol) was added to 4-[(E)-(hydroxyimino)methyl]-3-(trifluoromethyl)-N-[trimethylsilyl)methyl]benzamide (15.5 g, 49.4 mmol) in 1,2-Dichloroethane under cooling with ice. The reaction mixture was stirred at room temperature for 20 min and refluxed for 5 hours. Washed with H$_2$O, saturated NaHCO$_3$ and brine and dried over MgSO$_4$. After evaporation, the residue was purified with silicagel column chromatography (11.0 g, 75%).

1H-NMR (CDCl3) δ: 0.13 (9H, s), 2.99 (2H, d), 6.91 (1H, br d), 7.88 (1H, d), 8.06 (1H, d), 8.20 (1H, s).

Synthesis of 4-cyano-3-(trifluoromethyl)-N-[(trimethylsilyl)methyl]benzenecarbothioamide (compound 3-2)

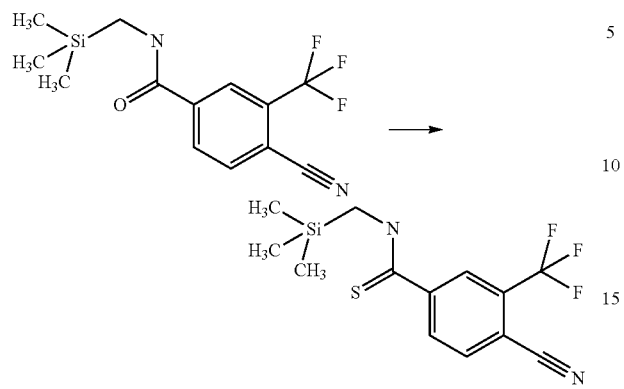

4-Cyano-3-(trifluoromethyl)-N-[(trimethylsilyl)methyl] benzamide (10.0 g, 33.2 mmol) and Lawson reagent (8.1 g, 19.9 mmol) in toluene was stirred at 85° C. for 1 hour. After evaporation, the residue was purified with silicagel column chromatography to give 9.1 g of the product (yield 86%).

1H-NMR (CDCl3) δ: 0.19 (9H, s), 3.55 (2H, d), 7.81-7.92 (3H, m), 8.07-8.07 (1H, m).

4-Cyano-3-methyl-N-[(trimethylsilyl)methyl]benzenecarbothioamide (compound 3-1) was synthesized by the same method

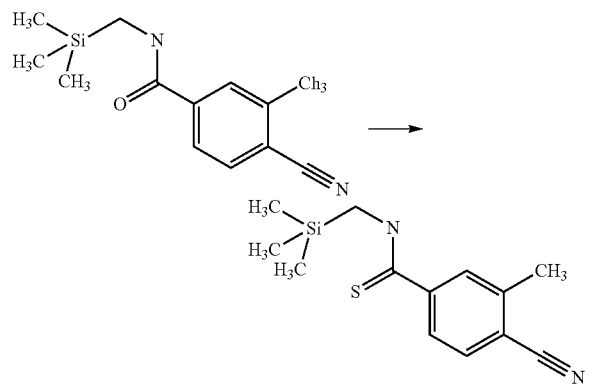

1H-NMR (CDCl3) δ: 0.18 (9H, s), 2.56 (3H, s), 3.53 (2H, d), 7.47-7.50 (1H, m), 7.58 (1H, d), 7.63 (1H, d), 7.71 (1H, br s).

Synthesis of 4-[3-(3,4,5-Trichlorophenyl)-3-(trifluoromethyl)-3,4-dihydro-2H-pyrrol-5-yl]-2-(trifluoromethyl)benzonitrile

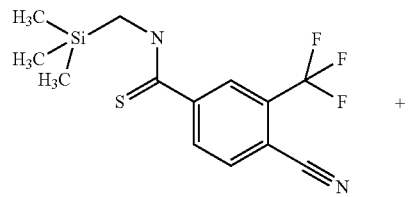

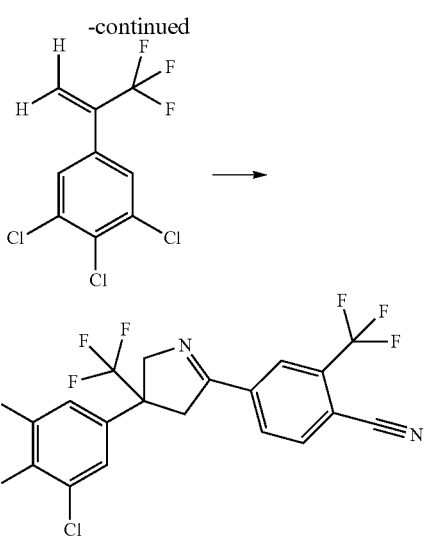

t-BuOK (0.39 g, 3.47 mmol) was added into 4-cyano-3-(trifluoromethyl)-N-[(trimethylsilyl)methyl]benzenecarbothioamide (1.00 g, 3.16 mmol) and methyl iodide (0.58 g, 4.10 mmol) in tetrahydrofuran at −60° C. and stirred for 30 minutes at the same temperature. Then diluted with t-BuOMe, and washed with saturated NaHCO3 aq. and brine, and dried over MgSO4. After evaporation, the residue was dissolved in tetrahydrofuran and cooled to −5° C. in an ice-acetone bath. To the mixture was slowly added dropwise a 1 M tetrahydrofuran solution of tetrabutylammonium fluoride (0.31 ml, 0.31 mmol) under Argon atmosphere. After stirring for 30 min at the same temperature, the reaction mixture was allowed to slowly warm up to room temperature. The mixture was then stirred for 20 hours at room temperature. Then 2 M HCl was added and extracted with EtOAc. The organic layer was washed with brine and dried over MgSO4. The solvent was evaporated and the residue was purified by column chromatography (0.82 g, 53%).

1H-NMR (CDCl3) δ: 3.47 (1H, d), 3.81 (1H, dd), 4.50 (1H, d), 4.97 (1H, dd), 7.40 (2H, s), 7.95 (1H, d), 8.13 (1H, dd), 8.29 (1H, s).

2-Methyl-4-[3-(3,4,5-trichlorophenyl)-3-(trifluoromethyl)-3,4-dihydro-2H-pyrrol-5-yl]benzonitrile was synthesized by the same method

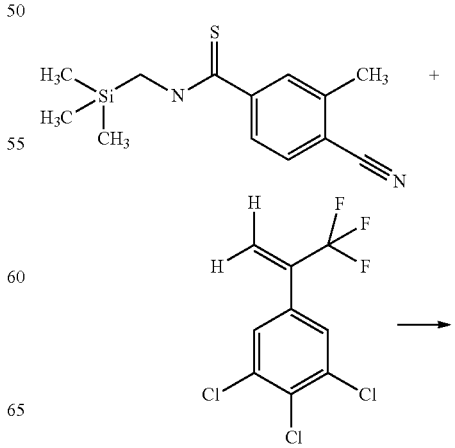

-continued

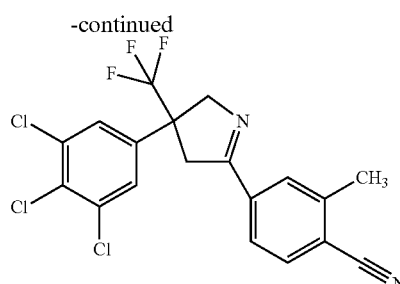

1H-NMR (CDCl3) δ: 2.61 (3H, s), 3.44 (1H, d), 3.79 (1H, dd), 4.46 (1H, d), 4.92 (1H, dd), 7.40 (2H, s), 7.67-7.75 (2H, m), 7.82 (1H, d).

Synthesis of 4-[3-(3,4,5-trichlorophenyl)-3-(trifluoromethyl)-3,4-dihydro-2H-pyrrol-5-yl]-2-(trifluoromethyl)benzoic acid

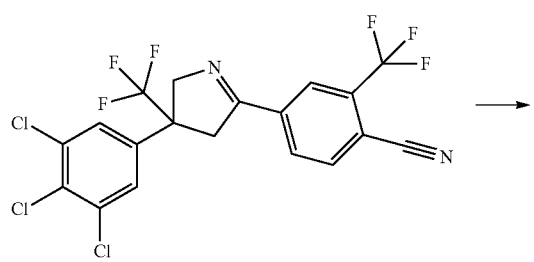

4-[3-(3,4,5-Trichlorophenyl)-3-(trifluoromethyl)-3,4-dihydro-2H-pyrrol-5-yl]-2-(trifluoromethyl)benzonitrile (0.82 g, 1.68 mmol) was dissolved in AcOH and suspended in conc. $H_2SO_4$—$H_2O$ mixture. The reaction mixture was stirred vigorously and refluxed for 26 hours. The reaction mixture was then poured to a mixture of ice and water. The resulting mixture was then extracted with EtOAc and the organic layer was washed with brine and dried over $Na_2SO_4$. The solvent was evaporated to obtain the product (0.70 g, 82%).

1H-NMR (CDCl3) δ: 3.52 (1H, d), 3.86 (1H, dd), 4.53 (1H, d), 4.98 (1H, dd), 7.42 (2H, s), 8.01 (1H, d), 8.09 (1H, dd), 8.25 (1H, s).

2-Methyl-4-[3(3,4,5-trichlorophenyl-1)-3-(trifluoromethyl)-3,4-dihydro-2H-pyrrol-5-yl]benzoic acid was synthesized by the same method

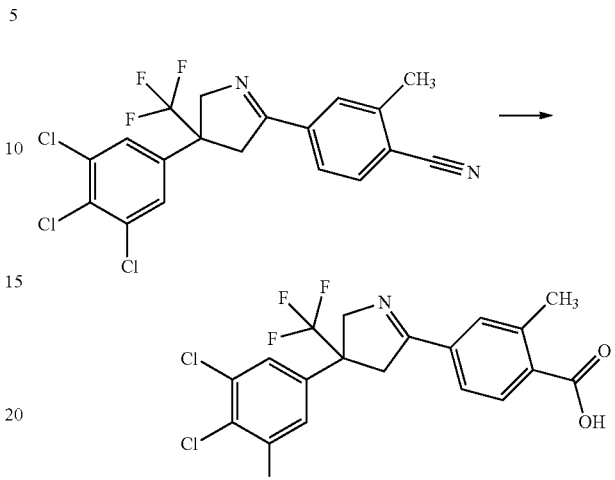

1H-NMR (CDCl3) δ: 2.71 (3H, s), 3.47 (1H, d), 3.83 (1H, dd), 4.47 (1H, d), 4.93 (1H, dd), 7.41 (2H, s), 7.73 (1H, dd), 7.77 (1H, s), 8.12 (1H).

The biological activity of the compounds according to the invention is illustrated through the following biological test examples:

Unless not mentioned otherwise, the test solutions were prepared as follows:

Containing as solvent: Dimethylformamide, 3 parts by weight; and as emulsifier: Polyoxyethylene alkyl phenyl ether, 1 part by weight To prepare the test solution, 1 part by weight of an active compound is mixed with the above-mentioned amount of solvent containing the above-mentioned amount of emulsifier, and the mixture is diluted with water to the desired concentration.

Biological Test Example 1

Test Against Tobacco Cutworm (*Spodoptera litura*) Larvae

Leaves of sweet potato were immersed in the test solution at the appropriate concentration, and the leaves were dried in air. The leaves were then placed in a petri dish having a diameter of 9 cm, and ten *Spodoptera litura* at third instar larvae were released therein. The petri dishes were placed in a temperature-controlled chamber at 25° C.

After 2 days and 4 days more sweet potato leaves were added. After 7 days, the number of dead larvae was counted and the insecticidal activity was calculated. An insecticidal activity of 100% means that all larvae were killed, whereas an insecticidal activity of 0% means that no larva was killed. In the current test, the results of two petri dishes for each treatment were averaged.

In the biological test example 1, the compounds Nos. 1-4, 1-7, 1-8, 1-9, 1-10, 1-11, 1-12, 1-16, 1-19, 1-20, 1-21, 1-104, 3-7 and 3-19 showed an insecticidal activity of 100% at an active compound concentration of 100 ppm.

Biological Test Example 2

Test Against Two-Spotted Spider Mite (*Tetranychus urticae*)

50 to 100 adult mites of *Tetranychus urticae* were inoculated to leaves of kidney bean at two-leaf stage planted in a pot of 6 cm in diameter. After one day, test solution at the appropriate concentration was sprayed thereon in a sufficient amount using a spray gun. After the spraying, the plant pot was placed inside a greenhouse, and after 7 days, the acaricidal activity was calculated. An acaricidal activity of 100% means that all mites were killed, whereas an acaricidal activity of 0% means that no mite was killed.

In the biological test example 2, the compound Nos. 1-7, 1-8, 1-9, 1-10, 1-11, 1-12, 1-16, 1-19, 1-20, 1-21 and 3-7 showed an acaricidal activity of 100% at an active compound concentration of 100 ppm.

Biological Test Example 3

Test Against Cucurbit Leaf Beetle (*Aulacophora femoralis*)

Leaves of cucumber were immersed in the test solution at the appropriate concentration, and the leaves were dried in air. The leaves were then put in a plastic cup containing sterilized black soil and five *Aulacophora femoralis* at second instar larvae were released in the cup. The cups were placed in a temperature-controlled chamber at 25° C. After 7 days, the number of dead larvae was counted, and the insecticidal activity was calculated. An insecticidal activity of 100% means that all larvae were killed, whereas an insecticidal activity of 0% means that no larva was killed.

In the biological test example 3, the compounds Nos. 1-4, 1-7, 1-8, 1-9, 1-10, 1-11, 1-12, 1-16, 1-19, 1-20, 1-21, 1-104, 3-7 and 3-19 showed an insecticidal activity of 100% at an active compound concentration of 100 ppm.

Biological Test Example 4

Test Against Organic Phosphorus Agent- and Carbamate Agent Resistant Green Peach Aphid (*Myzus persicae*)

50 to 100 head of organic phosphorous agent- and carbamate agent-resistant *Myzus persicae* were inoculated to leaves of eggplant at two-leaf stage, planted in a pot of 6 cm in diameter. After one day, test solution at the appropriate concentration was sprayed thereon in a sufficient amount using a spray gun. After the spraying, the plant pot was placed inside a greenhouse, and after 7 days, the insecticidal rate was calculated.

An insecticidal activity of 100% means that all aphids were killed, whereas an insecticidal activity of 0% means that no aphid was killed.

In the biological test example 4, the compounds Nos. 1-7, 1-9, 1-10, 1-12, 1-16, 1-19 and 1-21 showed an insecticidal activity of 100% at an active compound concentration of 100 ppm.

Comparative Examples in View of WO2009/080250

The following abbreviations were used:
RME: Rapeseed oil methyl ester, AS: Ammonium sulfate, dat: Days after treatment, a.i.: Active ingredient, r.h.: Relative humidity, Conc.: Concentration, Sorpol® SD and Sorpol® BDB (by Toho Chemical Industry Co. Ltd (CAS number 1330-20-7, Sorpol® SD: upper limit 13.000, Sorpol® BDB: upper limit 35.000) used as emulsifier.

*Spodoptera litura*—Root Soaking Test (PRODLI)
Insect: *Spodoptera litura* L2 stage;
Material: Culture media bottles for hydroponics: Plastic (A-PET) cups for test, square type;
Plant: Broccoli 5 leaf stage (ca. 12 cm high), soil around the roots was washed off just before the test;
Solvent pre-mixture "Sorpol SD" for root soaking test;
Sorpol SD: Sorpol BDB:Dimethylformamide=3:3:140
Procedure: Test solutions are prepared in the bottles at the appropriate concentration. The test plant root is dipped into the test solution in the bottle and kept in a test room. After 3 days, ⅓ part of the leaves of the plants is cut and put into the A-PET cup.

Into each test cup five larvae L2 are released, the cup is covered with a lid and stored at 25° C. and at a relative humidity of 50-60% and under 16L8D lighting conditions.

After the specified period of time the mortality in % is determined and the rate of death is calculated.

*Myzus persicae*—Spray Test (MYZUPE)
Insect: *Myzus persicae*-resistant strain, mixed population
Material: Paper labels
Plant: Eggplant seedling (*Solanum melongena* var. *Senryo 2gou*) 2 leaf age (4-5 weeks after sowing), transplanted into vinyl pots of 60 mm diameter
Solvent pre-mixture: Sorpol® SD: Sorpol® BDB:Dimethylformamide=3:3:14; 10 mg a.i. is solved with 0.05 ml solvent pre-mixture. Water for dilution contains RME and AS (1000 ppm each) or 0.1% of spreader. Solutions are diluted at the rate of 1:5 for limit concentration determination.

Procedure: 1 day before treatment aphids are inoculated onto the testing plants, about 50 aphids per leaf, 100 for 1 pot. A paper label is placed on each pot. Solutions are sprayed directly onto both insects and plants. After drying pots are placed in the greenhouse at 20° C.-25° C. and 50-60% relative humidity.

After the specified period of time the mortality in % is determined and the rate of death is calculated according to the following scheme/criteria:

| | |
|---|---|
| 100%: | All inoculated insects are dead |
| 98%: | 1 to 4 Insects survived/propagated |
| 90%: | 5 to 20 Insects survived/propagated |
| 60%: | Many insects survived/propagated, but less than in the untreated control, some dead aphids |
| 0%: | No difference from the untreated control. |

*Aulacophora femoralis*—Spray Test (AUACFE)
Insect: *Aulacophora femoralis* 2nd instar larvae from own culture;
Material: PET cups with 5 ml soil and A-PET lids
Plant: Cucumber (*Cucumis sativus* var. *Hanshiro*), cotyledon stage; 1 plant per pot;
Solvent pre-mixture: Sorpol® SD: Sorpol® BDB:Dimethylformamide=3:3:14;
10 mg a.i. solved with 0.05 ml solvent pre-mixture. Water for dilution contains RME and AS (1000 ppm each) or 0.1% of spreader. Solutions are diluted at the rate of 1:5 for limit concentration determination.

Procedure: Solutions are sprayed onto a plant. After drying, plants are cut and put on the soil in the testing cup. Five larvae L2 are released into each testing cup.

The testing cup is covered with the lid and stored at 25° C. and 50-60% r.h., 16L8D lighting conditions.

After the specified period of time, the mortality in % is determined according to the following scheme/criteria:

| | |
|---|---|
| 100%: | 5 Insects show apparent signs of death (change of color, decaying) |
| 50%: | 4-1 Insects show apparent signs of death. The living ones are apparently smaller than those in the control plot and/or feeding damage is clearly lesser than control plot |
| 0%: | 5 Insects are living, feeding, and growing just like control plot. |

*Panonychus citri*—Spray Test (METTCI)

Insect: *Panonychus citri*

Plant: Citrus plants, ca 8 cm height

Solvent pre-mixture: Sorpol® SD: Sorpol® BDB:Dimethylformamide=3:3:14

10 mg a i. is solved with 0.05 ml solvent pre-mixture.

Water for dilution contains RME and AS (1000 ppm each) or 0.1% of spreader. Solutions are diluted at the rate of 1:5 for limit concentration determination.

Procedure: 1 day before treatment mites were inoculated onto potted citrus plants, about 50 adults and some nymphs for 1 pot. The test solution is sprayed directly onto both mites and plants. After drying pots are stored at 25° C.

After the specified period of time mortality in % is determined by rating according to the following scheme/criteria.

| | |
|---|---|
| 100%: | All mites inoculated are dead |
| 98%: | 1 to 2 Mites survived/propagated |
| 90%: | 5 to 10 Mites survived/propagated |
| 60%: | Many mites survived/propagated, but less than the untreated control, some dead mites |
| 0%: | No difference from the untreated control. |

*Nephotettix cincticeps*-Spray Test (NEPHCl)

Insect: *Nephotettix cincticeps*-MR, resistant strain, 3rd-4th instar nymphs from own culture Plant: Rice seedlings (*Oryza sativa* var. *Tamanishiki*)

Material: ST-method container (200 ml desiccant polystyrene bottle) with a hole in the bottom sealed with metal mesh. The lid has a pit inside to keep desiccant, and it is used to sow rice seeds. The bottle is used upside down as "cover", the lid with seedling is called "base". Plastic stand-board with magnet labels to line the ST Bases up ("Stand")

Solvent pre-mixture: Sorpol® SD: Sorpol® BDB:Dimethylformamide=3:3:14 10 mg a i. is solved with 0.05 ml solvent pre-mixture. Water for dilution contains RME and AS (1000 ppm each) or 0.1% of spreader. Solutions are diluted at the rate of 1:5 for limit concentration determination.

Procedure: On a pit in the center of a base (originally the desiccant space) pieces of paper towel are placed. 20-30 germinated rice seeds are sown on the paper and moistened with water. The base is covered with a plastic cup and kept in an incubator at 30° C. for five days.

The base with rice seedlings is placed on the Stand. Each base is sprayed with the solution.

After drying twelve 3rd-4th instar nymphs of *Nephotettix cincticeps*-MR are put on the base and confined with the cover. The ST containers on the Stands are kept in the testing room at 25° C. and 50-60% r.h., 16L8D lighting conditions.

After the specified period of time mortality in % is determined by rating according to the following scheme/criteria: Counting living moving insects, calculate mortality in % by the formula: Mortality %=100×(10−number of insects found living)

*Bemisia tabacii*—Spray-Test (BEMIAR)

Insect: *Bemisia tabacii* biotype B

Material: Wooden labels

Plant: Tomato seedlings, 5 leaf stage in vinyl pots of 40 mm diameter

Solvent pre-mixture: Sorpol® SD: Sorpol® BDB:Dimethylformamide=3:3:14

10 mg a.i. is solved with 0.05 ml solvent pre-mixture. Water for dilution contains RME and AS (1000 ppm each) or 0.1% of spreader. Solutions are diluted at the rate of 1:5 for limit concentration determination.

Procedure: Solutions are sprayed to the plants. After drying treated pots are placed in the greenhouse where breeding BEMIAR for an infection-time of 24 h. Then the plants is placed in the testing room at 25° C. and 50-60% r.h., 16L8D lighting conditions.

After the specified period of time mortality in % is determined according to the following scheme/criteria:

| | |
|---|---|
| 100%: | All insects inoculated are dead. |
| 98%: | 1 to 4 Insects survived/propagated |
| 90%: | 5 to 20 Insects survived/propagated |
| 60%: | Many insects survived/propagated, but less than in the untreated control, some dead insects |
| 0%: | No difference from the untreated control |

*Tetranychus urticae*—Test (TETRUR)

Insect: *Tetranychus urticae*-S (sensible strain) mixed population from own culture Material: Paper labels Plant: Kidney bean seedlings (*Phaseolus vulgaris* var. *Serena*), 2 leaf stage (1 week after sowing)

Solvent pre-mixture: Sorpol® SD: Sorpol® BDB:Dimethylformamide=3:3:14

10 mg a i. is solved with 0.05 ml solvent pre-mixture.

Water for dilution contains RME and AS (1000 ppm each) or 0.1% of spreader. Solutions are diluted at the rate of 1:5 for limit concentration determination.

Procedure: 1 day before treatment the apex parts of testing plants are pruned. Mites are inoculated onto the testing plants, about 20 adults per leaf, 40 adults and some nymphs for 1 pot. A paper label is placed on each pot. The solution is sprayed onto mites and plants. After drying pots are placed in the greenhouse, temperature 20° C.-25° C.

After the specified period of time mortality in % is determined according to the following scheme/criteria:

| | |
|---|---|
| 100%: | All mites inoculated are dead. |
| 98%: | 1 to 4 Mites survived/propagated |
| 90%: | 5 to 20 Mites survived/propagated |
| 60%: | Many mites survived/propagated, but less than the untreated control, some dead mites |
| 0%: | No difference from the untreated control |

*Plutella xylostella*—Spray Test (PLUTXY)

Insect: *Plutella xylostella* 3rd instar larvae from own culture

Material: A-PET cup, A-PET lids

Plant: Broccoli 5 leaf stage

Solvent pre-mixture: Sorpol® SD: Sorpol® BDB:Dimethylformamide=3:3:14

10 mg a i. is solved with 0.05 ml solvent pre-mixture

Water for dilution contains RME and AS (1000 ppm each) or 0.1% of spreader. Solutions are diluted at the rate of 1:5 for limit concentration determination.

Procedure: Broccoli seedlings of 4-5 leaf stage planted in a vinyl pot (9 cm diameter) are sprayed with the solution. After drying half of the leaves of the plants are cut and put into a A-PET cup. Ten larvae of *Plutella xylostella* L3 are released in the cup and the dish is placed at 25° C. After 4 days another half leaf is cut and added to the dish. After the specified period of time mortality in % is determined according to the figures of mortality used for evaluation.

1 larva dead: 20% Efficacy 5 larvae dead: 100% Efficacy

*Adoxophyes honmai*—Test (ADXPFA)

Insect: *Adoxophyes honmai* from own culture

Material: 1 A-PET cup with lid

Food agent: 4.5 g of artificial diet powder Silkmate-Kantan-3®

Solvent pre-mixture: Sorpol® SD: Sorpol® BDB:Dimethylformamide=3:3:14

10 mg a i. is solved with 0.05 ml solvent pre-mixture. Water for dilution contains RME and AS (1000 ppm each) or 0.1% of spreader. Solutions are diluted at the rate of 1:5 for limit concentration determination.

Procedure: 4.5 g of artificial diet powder is put into a PET cup (10 cm diameter, 5 cm depth). The powder was leveled to make a layer in the bottom of the cup. 10 ml of a chemical solution is poured onto the powder and spreaded uniformly. The cup with treated diet powder is placed quiet to let the diet jell.

Into each testing cup five 3rd-instar larvae were released. The testing cup is closed with the lid and stored at 25° C. and 50-60% r.h., 16L8D lighting conditions.

After the specified period of time mortality in % is determined according to the following criteria:

1 larva dead: 20% Efficacy 5 larvae dead: 100% Efficacy

*Frankliniella occidentalis*—Spray-Test (FRANOC)

Insect: *Frankliniella occidentalis* from own culture

Plant: Cucumber seedlings, cotyledon stage

Solvent pre-mixture: Sorpol® SD: Sorpol® BDB:Dimethylformamide=3:3:14

10 mg a i. is solved with 0.05 ml solvent pre-mixture.

Water for dilution contains RME and AS (1000 ppm each) or 0.1% of spreader. Solutions are diluted at the rate of 1:5 for limit concentration determination.

Procedure: The solution is sprayed to a cucumber seedling. After drying, the plant is placed in a plastic stand. About fifty 1st-instar larvae were inoculated to the plant and covered with a cage. The plant is stored at 25° C.

After the specified period of time % efficacy is determined by rating feeding damages on the plant according to the following criteria:

| | |
|---|---|
| 100%: | The plant is completely protected. |
| 98%: | Slight damage |
| 90%: | About 10% of the leaf is damaged. |
| 60%: | Clear damage is observed, but significantly less than in the untreated control. |
| 0%: | No difference from the untreated control. |

The following compounds of WO 2009/080250 or WO2010/020522 and of the present invention were compared and the results are given as below:

TABLE 5

ExNo A10 of WO 2009/080250

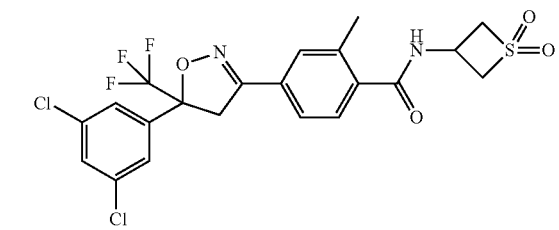

Compound T-1 according to the invention

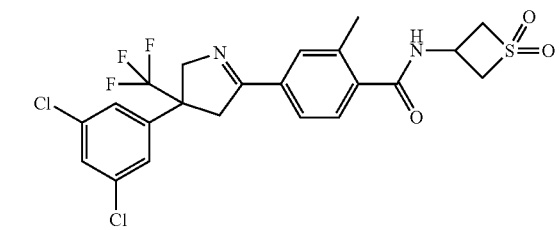

| Substance | Test | Conc. | Efficacy/day(s) of treatment |
|---|---|---|---|
| ExNo A10 of WO 2009/080250 | PRODLI | 20 ppm | 0%/4 dat |
| Compound T-1 according to the invention | PRODLI | 20 ppm | 100%/4 dat |

TABLE 6

ExNo A21 of WO 2009/080250

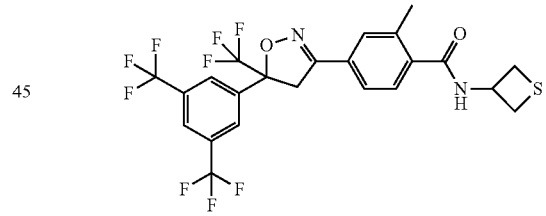

ExNo 1-19 according to the invention

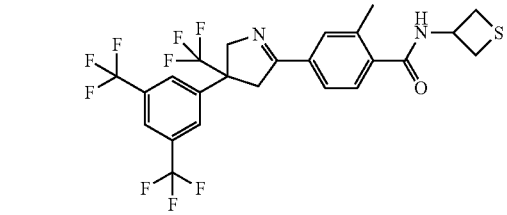

| Substance | Test | Conc. | Efficacy/day(s) of treatment |
|---|---|---|---|
| ExNo A21 of WO 2009/080250 | MYZUPE | 4 ppm | 60%/6 dat |
| | AUACFE | 0.8 ppm | 50%/6 dat |
| | METTCI | 4 ppm | 0%/7 dat |
| | NEPHCI | 20 ppm | 0%/7 dat |
| | BEMIAR | 100 ppm | 60%/14 dat |

TABLE 6-continued

| ExNo 1-19 according to the invention | MYZUPE | 4 ppm | 98%/6 dat |
|---|---|---|---|
| | AUACFE | 0.8 ppm | 100%/6 dat |
| | METTCI | 4 ppm | 60%/7 dat |
| | NEPHCI | 20 ppm | 20%/7 dat |
| | BEMIAR | 100 ppm | 100%/14 dat |

TABLE 7

ExNo A4 of WO 2009/080250

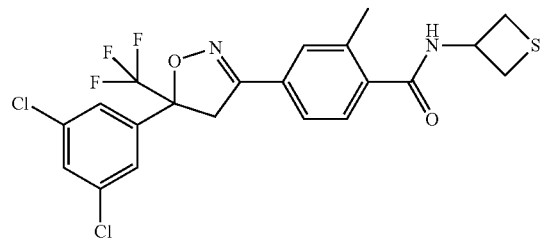

ExNo A49 of WO 2010/020522

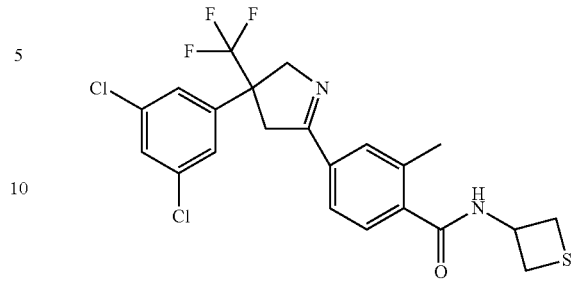

| Substance | Test | Conc. | Efficacy/day(s) of treatment |
|---|---|---|---|
| ExNo A-4 of WO 2009/080250 | PRODLI | 20 ppm | 80%/4 dat |
| | TETRUR | 0.16 ppm | 60%/2 dat |
| ExNo A49 of WO 2010/020522 | PRODLI | 20 ppm | 100%/4 dat |
| | TETRUR | 0.16 ppm | 90%/2 dat |

TABLE 8

Compound C-1 which is encompassed by WO 2009/080250

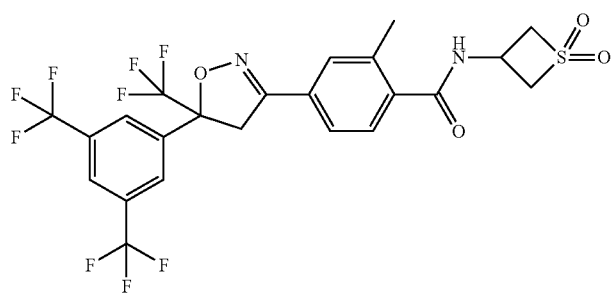

ExNo 1-21 according to the invention

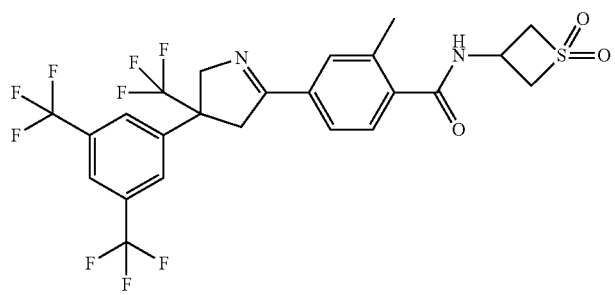

| Substance | Test | Conc. | Efficacy/day(s) of treatment |
|---|---|---|---|
| Compound C-1 which is encompassed by WO 2009/080250 | PLUTMA | 0.8 ppm | 80%/7 dat |
| | MYZUPE | 4 ppm | 60%/6 dat |
| | NEPHCI | 100 ppm | 70%/7 dat |
| | BEMIAR | 100 ppm | 60%/14 dat |
| ExNo 1-21 according to the invention | PLUTMA | 0.8 ppm | 100%/7 dat |
| | MYZUPE | 4 ppm | 98%/6 dat |
| | NEPHCI | 100 ppm | 90%/7 dat |
| | BEMIAR | 100 ppm | 98%/14 dat |

TABLE 9

ExNo A-23 of WO 2009/080250

ExNo 1-19 according to the invention

| Substance | Test | Conc. | Efficacy/day(s) of treatment |
|---|---|---|---|
| ExNo A-23 of WO 2009/080250 | ADXPFA | 0.8 ppm | 40%/2 dat |
|  | MYZUPE | 4 ppm | 60%/6 dat |
|  | NEPHCI | 20 ppm | 40%/7 dat |
|  | FRANOC | 0.16 ppm | 60%/7 dat |
| ExNo 1-19 according to the invention | ADXPFA | 0.8 ppm | 60%/2 dat |
|  | MYZUPE | 4 ppm | 90%/6 dat |
|  | NEPHCI | 20 ppm | 80%/7 dat |
|  | FRANOC | 0.16 ppm | 98%/7 dat |

The invention claimed is:

1. A compound of formula (I)

(I)

or a salt or N-oxide thereof, wherein
$A^1, A^2, A^3$, and $A^4$ independently represent a group C—H, C—$R^4$, or nitrogen;
L for is a single bond, —CH$_2$C(O)NH—, $C_1$-$C_8$alkylene, $C_1$-$C_8$haloalkylene, $C_2$-$C_8$alkenylene, $C_2$-$C_8$haloalkenylene, $C_2$-$C_8$alkynylene, or $C_2$-$C_8$haloalkynylene;
$R^1$ is hydrogen, $C_1$-$C_8$alkyl, $C_1$-$C_8$alkylcarbonyl, or $C_1$-$C_8$alkoxycarbonyl;
$R^2$ is hydrogen or $C_1$-$C_8$alkyl;
$R^3$ is aryl optionally substituted by one to four X or heterocyclyl optionally substituted by one to three X;
$Y^1, Y^2$, and $Y^3$ are each independently CR$^5$R$^6$, C=O, C=N—OR$^7$, N—R$^7$, S(O)$_n$, S=N—R$^7$, or S(O)=N—R$^7$; wherein n is 0, 1, or 2 and wherein $Y^1, Y^2$, and $Y^3$ are not CR$^5$R$^6$ at the same time;
$R^4$ is halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$ alkoxy, $C_1$-$C_8$haloalkoxy, $C_1$-$C_8$ alkoxycarbonyl, aryl optionally substituted by one to three R$^8$, heteroaryl optionally substituted by one to three R$^8$, or two adjacent R$^4$ together with the carbon atoms to which they are bound form a 5-membered ring, wherein the 5-membered ring comprises a —OCH=N—, —SCH=N—, —OCR$^8$=N—, or —SCR$^8$=N—;
X is halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl;
$R^5$ and $R^6$ are each independently hydrogen, halogen, $C_1$-$C_8$alkyl, or $C_1$-$C_8$haloalkyl;
$R^7$ is hydrogen, cyano, nitro, $C_1$-$C_8$alkyl, $C_1$-$C_8$haloalkyl, $C_3$-$C_6$-cycloalkyl-$C_1$-$C_4$alkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkyl wherein the aryl moiety is optionally substituted by one to three R$^9$, or heteroaryl-$C_1$-$C_4$alkyl wherein the heteroaryl moiety is optionally substituted by one to three R$^9$;
$R^8$ is halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl; and
$R^9$ is hydrogen, halogen, cyano, nitro, $C_1$-$C_8$alkyl, $C_1$-$C_8$haloalkyl, $C_1$-$C_8$alkoxy, $C_1$-$C_8$haloalkoxy, or $C_1$-$C_8$alkoxycarbonyl;
with the proviso that the compound of formula (I) is not:
(a) a compound wherein $R^3$ is 3,5-dichlorophenyl, $A^1$ is C—CH$_3$, $A^2, A^3$, and $A^4$ are each C—H, $R^1$ is H, L is a single bond, $Y^1$ and $Y^3$ are each CH$_2$, $Y^2$ is SO$_2$, and $R^2$ is H;
(b) a compound wherein $R^3$ is 3,5-dichlorophenyl, $A^1$ is C—CH$_3$, $A^2, A^3$, and $A^4$ are each C—H, $R^1$ is H, L is a single bond, $Y^1$ and $Y^3$ are each CH$_2$, $Y^2$ is S, and $R^2$ is CH$_3$;
(c) a compound wherein $R^3$ is 3,5-dichlorophenyl, $A^1$ is C—CH$_3$, $A^2, A^3$, and $A^4$ are each C—H, $R^1$ is H, L is a single bond, $Y^1$ and $Y^3$ are each CH$_2$, $Y^2$ is SO, and $R^2$ is H; and
(d) a compound wherein $R^3$ is 3,5-dichlorophenyl, $A^1$ is C—CH$_3$, $A^2, A^3$, and $A^4$ are each C—H, $R^1$ is H, L is a single bond, $Y^1$ and $Y^3$ are each CH$_2$, $Y^2$ is S, and $R^2$ is H.

2. The compound of claim 1, wherein $A^1$ is C—R$^4$, $A^2$ is C—H, $A^3$ is C—H, and $A^4$ is C—H.

3. The compound of claim 1, wherein $R^3$ is phenyl or pyridyl either of which is substituted by one to three X.

4. The compound of claim 1, wherein $Y^1, Y^2$, and $Y^3$ are each independently CR$^5$R$^6$, S(O)$_n$, S=N—R$^7$, or S(O)=N—R$^7$, wherein $Y^1, Y^2$, and $Y^3$ are not CR$^5$R$^6$ at the same time.

5. The compound of claim 1, wherein $Y^2$ is S(O)=N—R$^7$ or S(O)$_n$ and $Y^1$ and $Y^3$ are independently CR$^5$R$^6$.

6. A method for the preparation of a compound of formula (I) as claimed in claim 1, comprising reacting a compound of formula (II)

(II)

wherein
A$^1$, A$^2$, A$^3$, and A$^4$ are as defined in claim 1;
R$^{10}$ is hydrogen or C$_1$-C$_8$ alkyl; and
T is CN, methyl, C$_1$-C$_8$ alkoxycarbonyl, or a chemical group having the following formula

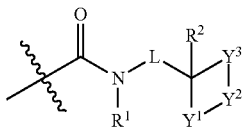

wherein L, R$^1$, R$^2$, Y$^1$, Y$^2$, and Y$^3$ are as defined in claim 1, with a compound of formula (V)

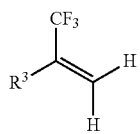
(V)

wherein R$^3$ is as defined in claim 1, in the presence of a fluorine reagent.

7. A compound of formula (II)

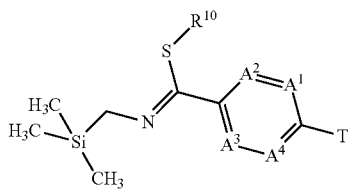
(II)

wherein
A$^1$, A$^2$, A$^3$, and A$^4$ independently represent a group C—H, C—R$^4$, or nitrogen;
R$^{10}$ is hydrogen or C$_1$-C$_8$alkyl;
T is CN, methyl, C$_1$-C$_8$alkoxycarbonyl, or a chemical group G having the following formula

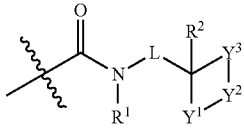

wherein
L is a single bond, —CH$_2$C(O)NH—, C$_1$-C$_8$alkylene, C$_1$-C$_8$haloalkylene, C$_1$-C$_8$alkenylene, C$_2$-C$_8$haloalkenylene, C$_2$-C$_8$alkynylene, or C$_7$-C$_8$haloalkynylene;
R$^1$ is hydrogen, C$_1$-C$_8$alkyl, C$_1$-C$_8$alkylcarbonyl, or C$_1$-C$_8$alkoxycarbonyl;
R$^2$ is hydrogen or C$_1$-C$_8$alkyl; and
Y$^1$, Y$^2$, and Y$^3$ are each independently CR$^5$R$^6$, C=O, C=N—OR$^7$, N—R$^7$, S(O)$_n$, S=N—R$^7$, or S(O)=N—R$^7$; wherein n is 0, 1, or 2 and wherein Y$^1$, Y$^2$, and Y$^3$ are not CR$^5$R$^6$ at the same time.

8. A method for controlling unwanted plant pests comprising allowing one or more compounds of the formula (I) according to claim 1 to act on the plant pests, their surroundings, or their habitat.

9. The compound of claim 1, wherein A$^1$ is C—H, A$^2$ is C—H, A$^3$ is C—H, and A$^4$ is C—R$^4$.

10. The compound of claim 1, wherein R$^3$ is 3,5-bis(trifluoromethyl)-phenyl, 3,5-dibromo-phenyl, 3,5-dichloro-phenyl, 3,4,5-trichloro-phenyl, 3-chloro-5-trifluoromethyl-phenyl, or 3,4-dichloro-5-trifluoromethyl-phenyl.

11. The compound of claim 1, wherein R$^3$ is 2,6-dichloro-pyridin-4-yl or 2,6-bis(trifluoromethyl)pyridin-4-yl.

12. The compound of claim 1, selected from the group consisting of:
N-(thietan-3-yl)-4-[3-(3,4,5-trichlorophenyl)-3-(trifluoromethyl)-3,4-dihydro-2H-pyrrol-5-yl]-2-(trifluoromethyl)benzamide;
4-{3-[3,5-Bis(trifluoromethyl)phenyl]-3-(trifluoromethyl)-3,4-dihydro-2H-pyrrol-5-yl}-N-(thietan-3-yl)-2-(trifluoromethyl)benzamide;
4-{3-[3,5-Bis(trifluoromethyl)phenyl]-3-(trifluoromethyl)-3,4-dihydro-2H-pyrrol-5-yl}-2-methyl-N-(thietan-3-yl)-2-(trifluoromethyl)benzamide;
N-(1,1-dioxidothietan-3-yl)-2-methyl-4-[3-(3,4,5-trichlorophenyl)-3-(trifluoromethyl)-3,4-dihydro-2H-pyrrol-5-yl]benzamide;
4-{3-[3,5-Bis(trifluoromethyl)phenyl]-3-(trifluoromethyl)-3,4-dihydro-2H-pyrrol-5-yl}-N-(1,1-dioxidothietan-3-yl)-2-methylbenzamide; and
N-(1,1-Dioxidothietan-3-yl)-4-[3-(3,4,5-trichlorophenyl)-3-(trifluoromethyl)-3,4-dihydro-2H-pyrrol-5-yl]-2-(trifluoromethyl)benzamide.

* * * * *